US010697967B2

(12) United States Patent
Liu et al.

(10) Patent No.: US 10,697,967 B2
(45) Date of Patent: *Jun. 30, 2020

(54) METHODS FOR PREDICTING RESPONSE OF TRIPLE-NEGATIVE BREAST CANCER TO THERAPY

(71) Applicant: Société des Produits Nestlé S.A., Vevey (CH)

(72) Inventors: Xinjun Liu, San Diego, CA (US); Phillip Kim, Irvine, CA (US); Richard Kirkland, San Diego, CA (US); Tani Lee, San Diego, CA (US); Belen Ybarrondo, San Diego, CA (US); Sharat Singh, Rancho Santa Fe, CA (US)

(73) Assignee: Société des Produits Nestlé S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/270,998

(22) Filed: Sep. 20, 2016

(65) Prior Publication Data

US 2017/0227542 A1   Aug. 10, 2017

Related U.S. Application Data

(63) Continuation of application No. 13/545,947, filed on Jul. 10, 2012, now Pat. No. 9,488,654, which is a continuation of application No. PCT/US2011/021026, filed on Jan. 12, 2011.

(60) Provisional application No. 61/351,838, filed on Jun. 4, 2010, provisional application No. 61/328,602, filed on Apr. 27, 2010, provisional application No. 61/325,624, filed on Apr. 19, 2010, provisional application No. 61/294,433, filed on Jan. 12, 2010.

(51) Int. Cl.
G01N 33/574   (2006.01)

(52) U.S. Cl.
CPC ... *G01N 33/57415* (2013.01); *G01N 2333/71* (2013.01); *G01N 2333/91205* (2013.01); *G01N 2800/52* (2013.01)

(58) Field of Classification Search
CPC .................................................. G01N 2800/52
See application file for complete search history.

(56) References Cited

U.S. PATENT DOCUMENTS

| 8,163,499 B2 | 4/2012 | Singh et al. |
| 2006/0263434 A1 | 11/2006 | Desai et al. |
| 2011/0071042 A1 | 3/2011 | Kim et al. |

FOREIGN PATENT DOCUMENTS

| WO | WO-2008036802 A2 * | 3/2008 | ....... G01N 33/54306 |
| WO | 2008/088854 A2 | 7/2008 | |
| WO | 2009/042613 | 4/2009 | |
| WO | 2009/108637 A1 | 9/2009 | |
| WO | 2010/132723 A1 | 11/2010 | |
| WO | 2012/010552 A1 | 1/2012 | |

OTHER PUBLICATIONS

Cleator et al. Triple-negative breast cancer: therapeutic options. Lancet Oncology, vol. 8, pp. 235-244, Mar. 2007. (Year: 2007).*
Fleisher et al. Current advances in biomarkers for targeted therapy in triple-negative breast cancer. Breast Cancer—Targets and Therapy, vol. 8, pp. 183-197, Oct. 2016. (Year: 2016).*
Nogi et al. EGFR as paradoxical predictor of chemosensitivity and outcome among triple-negative breast cancer. Oncology Reports, vol. 21, pp. 413-417, Feb. 2009 (Year: 2009).*
Oliveras-Ferraros et al. Growth and molecular interactions of anti-EGFR antibody cetuximab and the DNA cross-linking agent cisplatin in gefitinib-resistant MDA-MB-468 cells. International Journal of Oncology, vol. 33, pp. 1165-1176, 2008. (Year: 2008).*
Haab, BB. Antibody arrays in cancer research. Molecular & Cellular Proteomics, vol. 4, No. 4, pp. 377-383, 2005. (Year: 2005).*
Hu et al. Non-parametric quantification of protein lysate arrays. Bioinformatics, vol. 23, No. 15, pp. 1986-1994, 2007 (Year: 2007 ).*
Puputti et al. Amplification of KIT, PDGFRA, VEGFR2, and EGFR in gliomas. Molecular Cancer Research, vol. 4, No. 12, pp. 927-934, Dec. 2006. (Year: 2006).*
Garcia et al. Poor prognosis in breast carcinomas correlates with increased expression of targetable CD146 and c-Met and with proteomic basal-like phenotype. Human Pathology, vol. 38, pp. 830-841, 2007. (Year: 2007).*
Arslan, C. et al., "Pharmacotherapy of triple-negative breast cancer," Expert Opinion in Pharmacotherapy, 10(13):2081-2093, 2009.
Dawson, S.J. et al., "Triple negative breast cancers: clinical and prognostic implications," Eur. J. Cancer, 45:27-40, 2009.
Dent, R. et al., "Triple-Negative Breast Cancer: Clinical Features and Patterns of Recurrence," Clin Cancer Res. 13(15 Pt 1):4429-4434, 2007.
Dizdar, O. et al., "Dasatinib may also inhibit c-kit in triple negative breast cancer cell lines," Breast Cancer Res. Treat., 107:303, 2008.
Gainford, C. et al., "Phase I Trial of Docetaxel (T) and Cisplatin (P) as First-Line Chemotherapy for Metastatic Breast Cancer (MBC)," Proc Am Soc Clin Oncol., 19(113):Abstract 439, 2000.
Gradishar, W. J. et al., "Phase III Trial of Nanoparticle Albumin-Bound Paclitaxel Compared With Polyethylated Castor Oil-Based Paclitaxel in Women With Breast Cancer," J Clin Oncol., 23(31):7794-7803, 2005.

(Continued)

*Primary Examiner* — Jennifer Dunston
(74) *Attorney, Agent, or Firm* — Kilpatrick Townsend & Stockton LLP

(57) ABSTRACT

The present invention provides compositions and methods for detecting the expression and/or activation levels of components of signal transduction pathways in tumor cells such as triple-negative metastatic breast tumor cells. Information on the expression and/or activation levels of components of signal transduction pathways derived from use of the present invention can be used for cancer diagnosis, prognosis, and in the design of cancer treatments.

16 Claims, 14 Drawing Sheets

(56) References Cited

OTHER PUBLICATIONS

Hamilton, E. et al., "SPARC, EGFR, and VEGFR expression may predict response to NAB-paclitaxel/carboplatin/bevacizumab chemotherapy in triple-negative metastatic breast cancer," 46th American Society of Clinical Oncology Annual Meeting; Chicago, IL; Saturday, Jun. 5, 2010; 2:00 PM-6:00 PM; S Hall A2; Poster 35B.
Hamilton, E. et al., "Nab-paclitaxel/bevacizumab/carboplatin chemotherapy in first-line triple negative metastatic breast cancer," Clinical Breast Cancer, 13(6):416-420, 2013.
Kim, P. et al., "Highly sensitive proximity mediated immunoassay reveals HER2 status conversion in the circulating tumor cells of metastatic breast cancer patients," Proteome Science, 9:75, 2011, Printed as pp. 1/15-15/15.
Kurebayashi, J., "Possible treatment strategies for triple-negative breast cancer on the basis of molecular characteristics.," Breast Cancer, 16(4):275-280, 2009.
Law, J. et al., "Phosphorylated insulin-like growth factor-1/insulin receptor is present in all breast cancer subtypes and is related to poor survival," Cancer Res., 68(24):10238-10246, 2008.
Miles, D. et al., "Final Overall Survival (OS) Results from the Randomised, Double-Blind, Placebo-Controlled, Phase III AVADO Study of Bevacizumab (BV) plus Docetaxel (D) compared with placebo (PL) plus D for the first-line treatment of locally recurrent (LR) or metastatic Breast Cancer (mBC)," Cancer Res. 69(24S):495s, Abstract 41, 2009.
Miller, K. et al., "Paclitaxel plus Bevacizumab versus Paclitaxel Alone for Metastatic Breast Cancer," N Engl J Med. 357(26):2666-2676, 2007.
O'Shaughnessy, J., "Extending Survival with Chemotherapy in Metastatic Breast Cancer," Oncologist 10(Suppl 3):20-29, 2005.
Perez, E. et al., "A Phase II Study of Paclitaxel plus Carboplatin as First-Line Chemotherapy for Women with Metastatic Breast Carcinoma," Cancer 88(1):124-131, 2000.
Perez, E. et al., "A Phase II Trial of Docetaxel and Carboplatin as First-Line Chemotherapy for Metastatic Breast Cancer: NCCTG Study N9932," Oncology 69(2):117-121, 2005.
Perez, E., "Carboplatin in Combination Therapy for Metastatic Breast Cancer," Oncologist 9(5):518-527, 2004.
Ritz, C. and Streibig, J., "Bioassay Analysis using R," J. Statistical Software, 12:1-22, 2005.
Robert, N. et al., "RIBBON-1: Randomized, double-blind, placebo-controlled, phase III trial of chemotherapy with or without bevacizumab (B) for first-line treatment of HER2-negative locally recurrent or metastatic breast cancer (MBC)," J Clin Oncol. 27(15 suppl):42s, Abstract 1005, 2009.
Rydén, L. et al., "Epidermal growth factor receptor and vascular endothelial growth factor receptor 2 are specific biomarkers in triple-negative breast cancer. Results from a controlled randomized trial with long-term follow-up," Breast Cancer Res. Treat., 120(2):491-498, 2010.
Rydén, L. et al., "Vascular endothelial growth factor receptor 2 is a significant negative prognostic biomarker in triple-negative breast cancer: results from a controlled randomised trial of premenopausal breast cancer," Cancer Research, 69(2): Suppl. 1, 2009, Abstract #1087, printed as pp. 1/3-3/3.
Tan, A. et al., "Therapeutic strategies for triple-negative breast cancer," The Cancer Journal, 14(6):343-351, 2008.

\* cited by examiner

| Sorted by name | | Sorted by p value | | PFS, high vs low | | | |
|---|---|---|---|---|---|---|---|
| Marker | t test p value | Marker | t test p value | Marker | Avg wks low | Avg wks high | Wks diff |
| AKT.P | 0.683 | cKIT.T | 0.036 | cKIT.T | 42.1 | 20.7 | 21.4 |
| CK | 0.511 | VEGFR2.T | 0.056 | VEGFR2.T | 39.9 | 20.9 | 19.0 |
| cKIT.P | 0.266 | HER1.T | 0.138 | HER1.T | 23.4 | 36.8 | -13.4 |
| cKIT.T | 0.036 | IGF1R.P | 0.173 | IGF1R.P | 36.4 | 24.1 | 12.2 |
| cMET.P | 0.910 | cKIT.P | 0.266 | cKIT.P | 35.1 | 24.8 | 10.2 |
| cMET.T | 0.608 | IGF1R.T | 0.401 | IGF1R.T | 37.0 | 27.7 | 9.4 |
| HER1.P | 0.444 | HER1.P | 0.444 | HER1.P | 36.0 | 27.7 | 8.3 |
| HER1.T | 0.138 | CK | 0.511 | CK | 35.3 | 28.4 | 7.0 |
| HER2.P | 0.861 | HER2.T | 0.589 | HER2.T | 34.8 | 29.0 | 5.8 |
| HER2.T | 0.589 | cMET.T | 0.608 | cMET.T | 34.7 | 29.1 | 5.5 |
| HER3.P | 0.861 | AKT.P | 0.683 | AKT.P | 34.2 | 29.6 | 4.6 |
| HER3.T | 0.855 | PI3K.P | 0.733 | PI3K.P | 34.4 | 30.4 | 4.1 |
| IGF1R.P | 0.173 | MAPK.P | 0.733 | MAPK.P | 34.4 | 30.4 | 4.1 |
| IGF1R.T | 0.401 | HER3.T | 0.855 | HER3.T | 33.0 | 31.0 | 2.0 |
| MAPK.P | 0.733 | HER2.P | 0.861 | HER2.P | 31.2 | 33.1 | -1.9 |
| PI3K.P | 0.733 | HER3.P | 0.861 | HER3.P | 31.2 | 33.1 | -1.9 |
| VEGFR2.T | 0.056 | cMET.P | 0.910 | cMET.P | 31.9 | 32.7 | -0.8 |

*FIG. 10*

| Sorted by name | | Sorted by p value | | PFS, high vs low | | | |
|---|---|---|---|---|---|---|---|
| Marker | Wilcoxon p value | Marker | Wilcoxon p value | Marker | Avg wks low | Avg wks high | Wks diff |
| AKT.P | 0.277 | VEGFR2.T | 0.033 | VEGFR2.T | 39.9 | 20.9 | 19.0 |
| CK | 1.000 | cKIT.T | 0.074 | cKIT.T | 42.1 | 20.7 | 21.4 |
| cKIT.P | 0.721 | AKT.P | 0.277 | AKT.P | 34.2 | 29.6 | 4.6 |
| cKIT.T | 0.074 | HER1.T | 0.404 | HER1.T | 23.4 | 36.8 | -13.4 |
| cMET.P | 0.509 | HER1.P | 0.423 | HER1.P | 36.0 | 27.7 | 8.3 |
| cMET.T | 0.888 | IGF1R.T | 0.481 | IGF1R.T | 37.0 | 27.7 | 9.4 |
| HER1.P | 0.423 | cMET.P | 0.509 | cMET.P | 31.9 | 32.7 | -0.8 |
| HER1.T | 0.404 | IGF1R.P | 0.525 | IGF1R.P | 36.4 | 24.1 | 12.2 |
| HER2.P | 0.743 | HER2.T | 0.673 | HER2.T | 34.8 | 29.0 | 5.8 |
| HER2.T | 0.673 | cKIT.P | 0.721 | cKIT.P | 35.1 | 24.8 | 10.2 |
| HER3.P | 0.743 | HER2.P | 0.743 | HER2.P | 31.2 | 33.1 | -1.9 |
| HER3.T | 0.888 | HER3.P | 0.743 | HER3.P | 31.2 | 33.1 | -1.9 |
| IGF1R.P | 0.525 | cMET.T | 0.888 | cMET.T | 34.7 | 29.1 | 5.5 |
| IGF1R.T | 0.481 | HER3.T | 0.888 | HER3.T | 33.0 | 31.0 | 2.0 |
| MAPK.P | 0.962 | MAPK.P | 0.962 | MAPK.P | 34.4 | 30.4 | 4.1 |
| PI3K.P | 0.962 | PI3K.P | 0.962 | PI3K.P | 34.4 | 30.4 | 4.1 |
| VEGFR2.T | 0.033 | CK | 1.000 | CK | 35.3 | 28.4 | 7.0 |

*FIG. 11*

METHODS FOR PREDICTING RESPONSE OF TRIPLE-NEGATIVE BREAST CANCER TO THERAPY

CROSS-REFERENCES TO RELATED APPLICATIONS

This application is a continuation of Ser. No. 13/545,947, filed Jul. 10, 2012, which is a continuation of PCT/US2011/021026, filed Jan. 12, 2011, which application claims priority to U.S. Provisional Application No. 61/294,433, filed Jan. 12, 2010, U.S. Provisional Application No. 61/325,624, filed Apr. 19, 2010, U.S. Provisional Application No. 61/328,602, filed Apr. 27, 2010, and U.S. Provisional Application No. 61/351,838, filed Jun. 4, 2010, the disclosures of which are herein incorporated by reference in their entirety for all purposes.

BACKGROUND OF THE INVENTION

The process of signal transduction in cells is responsible for a variety of biological functions including cell division and death, metabolism, immune cell activation, neurotransmission, and sensory perception to name but a few. Accordingly, derangements in normal signal transduction in cells can lead to a number of disease states such as diabetes, heart disease, autoimmunity, and cancer.

One well characterized signal transduction pathway is the MAP kinase pathway, which is responsible for transducing the signal from epidermal growth factor (EGF) to the promotion of cell proliferation in cells (see, FIG. 1 of PCT Publication No. WO2009/108637, the disclosure of which is herein incorporated by reference in its entirety for all purposes). EGF binds to a transmembrane receptor-linked tyrosine kinase, the epidermal growth factor receptor (EGFR), which is activated by the binding of EGF. The binding of EGF to EGFR activates the tyrosine kinase activity of the cytoplasmic domain of the receptor. One consequence of this kinase activation is the autophosphorylation of EGFR on tyrosine residues. The phosphorylated tyrosine residues on the activated EGFR provide a docking site for the binding of SH2 domain containing adaptor proteins such as GRB2. In its function as an adaptor, GRB2 further binds to a guanine nucleotide exchange factor, SOS, by way of an SH3 domain on GRB2. The formation of the complex of EGFR-GRB2-SOS leads to SOS activation of a guanine nucleotide exchange factor that promotes the removal of GDP from Ras. Upon removal of GDP, Ras binds GTP and becomes activated.

Following activation, Ras binds to and activates the protein kinase activity of RAF kinase, a serine/threonine-specific protein kinase. What follows is the activation of a protein kinase cascade that leads to cell proliferation. In outline, RAF kinase then phosphorylates and activates MEK, another serine/threonine kinase. Activated MEK phosphorylates and activates mitogen-activated protein kinase (MAPK). Among the targets for further phosphorylation by MAPK are 40S ribosomal protein S6 kinase (RSK). The phosphorylation of RSK by MAPK results in activation of RSK, which in turn phosphorylates ribosomal protein S6. Another known target of MAPK is the proto-oncogene, c-Myc, a gene important for cell proliferation, which is mutated in a variety of cancers. MAPK also phosphorylates and activates another protein kinase, MNK, which in turn phosphorylates the transcription factor, CREB. Indirectly, MAPK also regulates the transcription of the Fos gene, which encodes yet another transcription factor involved in cell proliferation. By altering the levels and activities of such transcription factors, MAPK transduces the original extracellular signal from EGF into altered transcription of genes that are important for cell cycle progression.

Given the central role that signal transduction pathways play in cell growth, it is not surprising that many cancers arise as a result of mutations and other alterations in signal transduction components that result in aberrant activation of cell proliferation pathways. For example, overexpression or hyperactivity of EGFR has been associated with a number of cancers, including glioblastoma multiforme, colon cancer, and lung cancer. This has prompted the development of anticancer therapeutics directed against EGFR, including gefitinib and erlotinib for lung cancer, and cetuximab for colon cancer.

Cetuximab is an example of a monoclonal antibody inhibitor, which binds to the extracellular ligand-binding domain of EGFR, thus preventing the binding of ligands which activate the EGFR tyrosine kinase. In contrast, gefitinib and erlotinib are small molecules which inhibit the intracellularly-located EGFR tyrosine kinase. In the absence of kinase activity, EGFR is unable to undergo autophosphorylation at tyrosine residues, which is a prerequisite for binding of downstream adaptor proteins, such as GRB2. By halting the signaling cascade in cells that rely on this pathway for growth, tumor proliferation and migration is diminished.

Additionally, other studies have shown that about 70% of human melanomas and a smaller fraction of other tumors have a point mutation (V599E) in the Raf gene which leads to persistent activation of the MAPK pathway (see, e.g., Davies et al., Nature, 417:949-954 (2002)). Such results suggest that mutations in particular signal transduction pathways may be characteristic of particular types of tumors and that such specific, altered signal transduction pathways may be a promising target for chemotherapeutic intervention.

Given that different cancer treatments, particularly cancer chemotherapy, may function either directly or indirectly by means of either blocking or activating cellular signal transduction pathways that are involved in cell proliferation or death, respectively, the activity of a given signal transduction pathway in a particular form of cancer may serve as a good indicator of the efficacy of various cancer treatments. Accordingly, in addition to fulfilling other needs, the present invention provides methods for predicting and evaluating the effectiveness of potential anticancer therapies for an individual patient. As such, the present invention provides methods for assisting a physician in selecting a suitable cancer therapy at the right dose and at the right time for every patient.

BRIEF SUMMARY OF THE INVENTION

The present invention provides compositions and methods for detecting the status (e.g., expression and/or activation levels) of components of signal transduction pathways in tumor cells (e.g., triple-negative breast tumor cells). Information on the expression and/or activation states of components of signal transduction pathways derived from practice of the present invention can be used for cancer diagnosis, prognosis, and in the design of cancer treatments.

In particular aspects, the present invention provides molecular markers (biomarkers) that enable the determination or prediction of whether a particular cancer can respond or is likely to respond favorably to one or more anticancer drugs such as, e.g., a combination of bevacizumab (Avastin®), carboplatin, and paclitaxel (e.g., Abraxane® or nabP) ("triplet therapy"). As described herein, it has been surprisingly found that biomarkers such as VEGFR2, c-KIT, HER1, and IGF-1R are particularly useful in determining or predicting the sensitivity, efficacy, or response of tumor cells such as triple-negative breast tumor cells to anticancer therapy such as triplet therapy.

In one aspect, the present invention provides a method for determining the sensitivity of a triple-negative tumor cell to therapy with an anticancer drug, the method comprising:
  (a) lysing the tumor cell to produce a cellular extract;
  (b) determining the expression level of VEGFR2, c-KIT, HER1, and/or IGF-1R in the cellular extract; and
  (c) comparing the expression level of VEGFR2, c-KIT, HER1, and/or IGF-1R in the cellular extract determined in step (b) to a reference expression level of VEGFR2, c-KIT, HER1, and/or IGF-1R,
  wherein the presence of a low level of VEGFR2 expression, a low level of c-KIT expression, a high level of HER1 expression, and/or a low level of IGF-1R expression in the cellular extract compared to the reference expression level indicates that the tumor cell is sensitive to the anticancer drug.

In some embodiments, the methods of the present invention may be useful to aid or assist in determining or predicting the sensitivity of a triple-negative tumor cell to therapy with an anticancer drug. In other embodiments, the methods of the present invention may be useful for improving the determination or prediction of the sensitivity of a triple-negative tumor cell to therapy with an anticancer drug.

In another aspect, the present invention provides a method for predicting the response of a triple-negative breast tumor to therapy with an anticancer drug, the method comprising:
  (a) lysing a tumor cell obtained from the triple-negative breast tumor to produce a cellular extract;
  (b) determining the expression level of VEGFR2, c-KIT, HER1, and/or IGF-1R in the cellular extract; and
  (c) comparing the expression level of VEGFR2, c-KIT, HER1, and/or IGF-1R in the cellular extract determined in step (b) to a reference expression level of VEGFR2, c-KIT, HER1, and/or IGF-1R,
  wherein the presence of a low level of VEGFR2 expression, a low level of c-KIT expression, a high level of HER1 expression, and/or a low level of IGF-1R expression in the cellular extract compared to the reference expression level is predictive of response to therapy with the anticancer drug.

In some embodiments, the methods of the present invention may be useful to aid or assist in determining or predicting the response of a triple-negative breast tumor to therapy with an anticancer drug. In other embodiments, the methods of the present invention may be useful for improving the determination or prediction of the response of a triple-negative breast tumor to therapy with an anticancer drug.

In a further aspect, the present invention provides a method for monitoring the response to therapy with an anticancer drug in a subject having a triple-negative breast tumor and receiving the anticancer drug, the method comprising:
  (a) lysing a tumor cell obtained from the triple-negative breast tumor to produce a cellular extract;
  (b) determining the expression level of VEGFR2, c-KIT, HER1, and/or IGF-1R in the cellular extract;
  (c) comparing the expression level of VEGFR2, c-KIT, HER1, and/or IGF-1R in the cellular extract determined in step (b) to a reference expression level of VEGFR2, c-KIT, HER1, and/or IGF-1R or to an expression level of VEGFR2, c-KIT, HER1, and/or IGF-1R at an earlier time during therapy; and
  (d) determining whether therapy with the anticancer drug should be continued or adjusted based upon the comparison in step (c).

In some embodiments, the methods of the present invention may be useful to aid or assist in monitoring the response of a triple-negative breast tumor to therapy with an anticancer drug. In other embodiments, the methods of the present invention may be useful for improving the monitoring of the response of a triple-negative breast tumor to therapy with an anticancer drug. In certain embodiments, the adjustment of therapy in step (d) comprises changing a subsequent dose of the anticancer drug or selecting an alternative anticancer drug.

Other objects, features, and advantages of the present invention will be apparent to one of skill in the art from the following detailed description and figures.

BRIEF DESCRIPTION OF THE DRAWINGS

FIG. 10 shows the results of a comparison between the Progression Free Survival (PFS) for the low and high sample groups for each marker.

FIG. 11 shows the results of another comparison between the PFS for the low and high sample groups for each marker.

Figure 1:
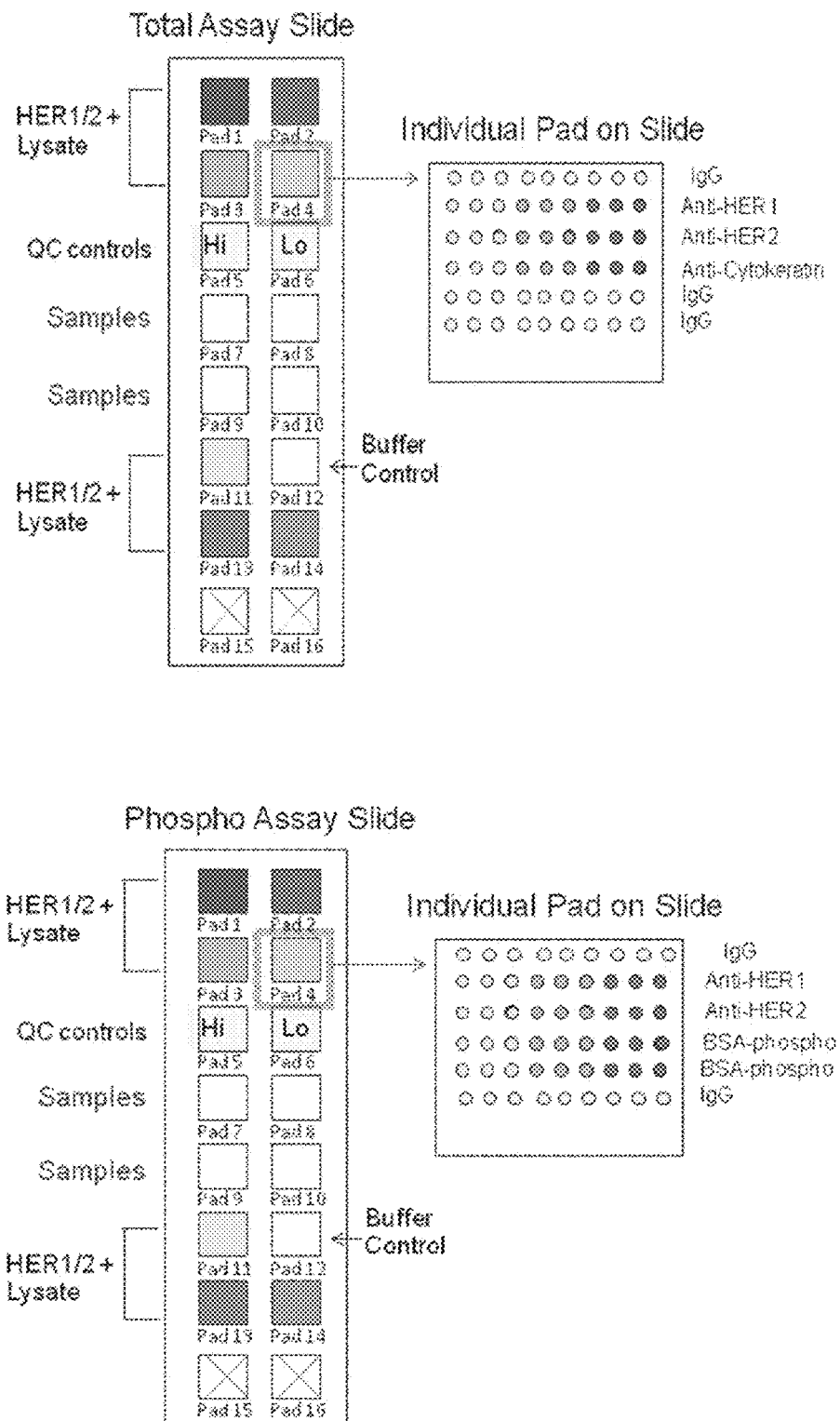
FIG. 1 shows the array designs of exemplary slide formats for analyzing total and phosphorylated HER1 and HER2 levels.

The figures and tables from PCT Publication No. WO 2010/132723 are herein incorporated by reference in their entirety for all purposes.

DETAILED DESCRIPTION OF THE INVENTION

I. Introduction

As described above, the activation of signal transduction pathways that are involved in cell proliferation and the deactivation of pathways that are involved in cell death are non-limiting examples of molecular features that characterize many different types of cancer. In many cases, the activity of particular signal transduction pathways, and components thereof, may serve as molecular signatures for a given type of cancer. Such activated components may further provide useful targets for therapeutic intervention. Accordingly, knowledge of the activity level of a particular signal transduction system within a cancer cell prior to, during, and after treatment provides a physician with highly relevant information that may be used to select an appropriate course of treatment to adopt. Furthermore, the continued monitoring of signal transduction pathways that are active in cancer cells as treatment progresses can provide the physician with additional information on the efficacy of treatment, prompting the physician to either continue a particular course of treatment or to switch to another line of treatment, when, for example, cancer cells have become resistant to treatment through further aberrations that activate either the same or another signal transduction pathway.

Accordingly, the present invention provides methods and compositions for detecting the expression and/or activation states of one or a plurality of deregulated signal transduction molecules in tumor tissue or extratumoral cells such as rare circulating cells of a solid tumor in a specific, multiplex, high-throughput assay. The invention also provides methods and compositions for the selection of appropriate therapy (single drugs or combinations of drugs) to down-regulate or shut down a deregulated signaling pathway. Thus, the invention may be used to facilitate the design of personalized therapies for cancer patients.

In certain embodiments, the ability to detect and identify tumor cells in the circulation through the determination of the activity of signal transduction pathways at the level of single cells is an important advantage of the present invention. Tumor cells are often found in the blood of patients with various early stages of cancer as "micrometastases" (disseminated tumor cells) and are also found in metastatic cancers. The number of tumor cells in blood will depend on the stage and type of tumor. While biopsies are typically obtained on primary tumors, most metastatic tumors are not biopsied, making molecular analysis of such tumor samples very difficult. During tumor metastasis, the most aggressive tumor cells leave the primary tumor and travel through the blood and lymphatic system to reach a distant location. Thus, circulating tumor cells from blood represent the most aggressive and homogenous population of tumor cells. However, the number of metastatic tumor cells in blood is frequently very low, varying from one to several thousand cells per milliliter of blood. The ability to isolate and assay signal transduction pathways in such rare cells and to apply this information toward more effective cancer treatments is one object of the present invention.

In particular embodiments, the multiplex, high-throughput immunoassays of the present invention (e.g., Collaborative Enzyme Enhanced Reactive ImmunoAssay (CEER), also known as the COllaborative Proximity ImmunoAssay (COPIA)) can detect the level of expression and/or activation of one or more signal transduction molecules in cells obtained from tumor tissue (e.g., FNA samples) or in circulating cells of a solid tumor at the single cell level. In fact, signal transduction molecules such as EGFR can be detected with a sensitivity of about 100 zeptomoles and a linear dynamic range of from about 100 zeptomoles to about 100 femtomoles. As such, single-cell detection of the expression and/or activation levels of one or multiple signal transducers in tumor cells facilitates cancer prognosis and diagnosis as well as the design of personalized, targeted therapies.

With regard to breast cancer, current testing options are unsatisfactory because treatment of both primary and metastatic tumors in a breast cancer patient is based on a one-time diagnosis from a biopsy sample taken during an early stage of the disease. In particular, therapeutic intervention for both the early and metastatic stages of breast cancer is based solely on the initial diagnosis from the biopsy sample taken during an early stage of the disease because of the impracticality of obtaining a biopsy sample from a metastatic cancer patient. However, breast tumors are evolving as a function of time and treatment such that temporal monitoring of breast tumors is critical for optimal management of breast cancer patients. For example, a change in the activation state of one or more of the ErbB (HER) family of receptor tyrosine kinases may affect therapy selection at recurrence. Indeed, discordance in HER-2 status between primary and metastatic cancer is common because up to 37% of all breast cancer patients change from a HER-2-negative primary tumor to HER-2-positive metastatic cancer. In addition, patients may have de novo resistance or develop acquired resistance to hormonal therapy due to HER-1 and/or HER-2 activation. In some instances, patients may have de novo resistance or develop acquired resistance to ErbB-targeted therapies due to the presence of tumor cells expressing p95HER-2. As a result, there is an unmet clinical need for assays to assist the clinician in prescribing the appropriate cancer therapy at the appropriate time because current technology lacks sensitivity and specificity, cannot be used to monitor patients on therapy, and do not utilize pathway profiling to guide individualized treatment decisions.

In contrast to currently available breast cancer testing options, the methods of the present invention enable the monitoring of breast cancer patients through all stages of the disease by providing a "real-time biopsy" of solid breast tumors using samples such as fine needle aspirates (FNAs) from the tumor and/or circulating tumor cells (CTCs) from blood. As a non-limiting example, the breast cancer assays described herein can be used in the initial diagnosis of breast cancer in a patient at an early stage of the disease. Selection of a suitable cancer therapy is guided by profiling the expression and/or activation levels of one or more specific signaling pathways with or without anticancer drugs using the single detection and proximity dual detection assays (e.g., CEER) described herein. Advantageously, the methods of the present invention can also be used to monitor the progression and/or regression of the disease because therapeutic intervention may be based on samples taken at any stage of the disease and analyzed using the single detection and proximity dual detection assays (e.g., CEER) described herein. As such, prediction, identification, and/or selection of suitable cancer therapies for the early and metastatic stages of breast cancer is guided by real-time diagnosis and an analysis of the expression and/or activation status of specific signaling pathway molecules.

The methods of the present invention are beneficially tailored to address key issues in cancer management and provide a higher standard of care for breast cancer patients (e.g., triple-negative metastatic breast cancer (TNMBC) patients) because they: (1) provide increased sensitivity (e.g., single cell detection can be achieved for detecting total and/or phosphorylated signal transduction molecules such as HER1 (EGFR), VEGFR2, and/or c-KIT); (2) provide increased specificity (e.g., three-antibody proximity assays enhance the specificity for detecting total and/or phosphorylated signal transduction molecules); (3) enable pathway profiling (e.g., expression and/or activation status of one or more specific signal transduction molecules can be detected in FNA or CTCs from patients); and (4) eliminate any issues with obtaining patient samples (e.g., assays can be performed on a few tumor cells). Although any sample may be used in the novel assays described herein, CTCs are particularly useful because they represent the most aggressive tumor cells, every tumor is known to shed CTCs, they can be the only source of residual tumors or hard-to-access metastatic tumors, and they are found in blood. As such, in certain embodiments, the methods of the present invention enable the serial sampling of breast tumor tissues, resulting in valuable information on changes occurring in tumor cells as a function of time and therapy and providing clinicians with a means to monitor rapidly evolving cancer pathway signatures.

In sum, the methods of the present invention advantageously provide accurate selection and monitoring of cancer patients (e.g., TNMBC patients) most likely to benefit from targeted therapy by performing pathway profiling on tumor cells using multiplexed, antibody-based single detection or proximity assays.

II. Definitions

As used herein, the following terms have the meanings ascribed to them unless specified otherwise.

The term "cancer" is intended to include any member of a class of diseases characterized by the uncontrolled growth of aberrant cells. The term includes all known cancers and neoplastic conditions, whether characterized as malignant, benign, soft tissue, or solid, and cancers of all stages and grades including pre- and post-metastatic cancers. Examples of different types of cancer include, but are not limited to, breast cancer; lung cancer (e.g., non-small cell lung cancer); digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; ovarian cancer; renal cancer (e.g., renal cell carcinoma); cancer of the central nervous system; skin cancer; lymphomas; choriocarcinomas; head and neck cancers; osteogenic sarcomas; and blood cancers. As used herein, a "tumor" comprises one or more cancerous cells. In one preferred embodiment, the breast tumor is derived from a subject with an invasive or in situ form of ductal carcinoma or lobular carcinoma. In another preferred embodiment, the breast tumor is derived from a subject with recurrent or metastatic breast cancer.

The term "analyte" includes any molecule of interest, typically a macromolecule such as a polypeptide, whose presence, amount (expression level), activation state, and/or identity is determined. In certain instances, the analyte is a signal transduction molecule such as, e.g., HER1 (EGFR), VEGFR2, or c-KIT.

The term "signal transduction molecule" or "signal transducer" includes proteins and other molecules that carry out the process by which a cell converts an extracellular signal or stimulus into a response, typically involving ordered sequences of biochemical reactions inside the cell. Examples of signal transduction molecules include, but are not limited to, receptor tyrosine kinases such as EGFR (e.g., EGFR/HER1/ErbB1, HER2/Neu/ErbB2, HER3/ErbB3, HER4/ErbB4), VEGFR1/FLT1, VEGFR2/FLK/KDR, VEGFR3/FLT4, FLT3/FLK2, PDGFR (e.g., PDGFRA, PDGFRB), c-KIT/SCFR, INSR (insulin receptor), IGF-1R, IGF-IIR, IRR (insulin receptor-related receptor), CSF-1R, FGFR 1-4, HGFR 1-2, CCK4, TRK A-C, c-MET, RON, EPHA 1-8, EPHB 1-6, AXL, MER, TYRO3, TIE 1-2, TEK, RYK, DDR 1-2, RET, c-ROS, V-cadherin, LTK (leukocyte tyrosine kinase), ALK (anaplastic lymphoma kinase), ROR 1-2, MUSK, AATYK 1-3, and RTK 106; truncated forms of receptor tyrosine kinases such as truncated HER2 receptors with missing amino-terminal extracellular domains (e.g., p95ErbB2 (p95m), p110, p95c, p95n, etc.); receptor tyrosine kinase dimers (e.g., p95HER2/HER3, p95HER2/HER2, HER2/HER2, HER2/HER3, HER1/HER2, HER2/HER3, HER2/HER4, etc.); non-receptor tyrosine kinases such as BCR-ABL, Src, Frk, Btk, Csk, Abl, Zap70, Fes/Fps, Fak, Jak, Ack, and LIMK; tyrosine kinase signaling cascade components such as AKT (e.g., AKT1, AKT2, AKT3), MEK (MAP2K1), ERK2 (MAPK1), ERK1 (MAPK3), PI3K (e.g., PIK3CA (p110), PIK3R1 (p85)), PDK1, PDK2, phosphatase and tensin homolog (PTEN), SGK3, 4E-BP1, P70S6K (e.g., p70 S6 kinase splice variant alpha I), protein tyrosine phosphatases (e.g., PTP1B, PTPN13, BDP1, etc.), RAF, PLA2, MEKK, JNKK, JNK, p38, Shc (p66), Ras (e.g., K-Ras, N-Ras, H-Ras), Rho, Racl, Cdc42, PLC, PKC, p53, cyclin D1, STAT1, STAT3, phosphatidylinositol 4,5-bisphosphate (PIP2), phosphatidylinositol 3,4,5-trisphosphate (PIP3), mTOR, BAD, p21, p27, ROCK, IP3, TSP-1, NOS, GSK-3β, RSK 1-3, JNK, c-Jun, Rb, CREB, Ki67, and paxillin; nuclear hormone receptors such as estrogen receptor (ER), progesterone receptor (PR), androgen receptor, glucocorticoid receptor, mineralocorticoid receptor, vitamin A receptor, vitamin D receptor, retinoid receptor, thyroid hormone receptor, and orphan receptors; nuclear receptor coactivators and repressors such as amplified in breast cancer-1 (AIB1) and nuclear receptor corepressor 1 (NCOR), respectively; and combinations thereof.

The term "activation state" refers to whether a particular signal transduction molecule is activated. Similarly, the term "activation level" refers to what extent a particular signal transduction molecule is activated. The activation state or level typically corresponds to the phosphorylation, ubiquitination, and/or complexation status or level of one or more (e.g., a plurality of) signal transduction molecules. Non-limiting examples of activation states (listed in parentheses) include: HER1/EGFR (EGFRvIII, phosphorylated (p-) EGFR, EGFR:Shc, ubiquitinated (u-) EGFR, p-EGFRvIII); ErbB2 (p-ErbB2, p95HER2 (truncated ErbB2), p-p95HER2, ErbB2:Shc, ErbB2:PI3K, ErbB2: EGFR, ErbB2:ErbB3, ErbB2:ErbB4); ErbB3 (p-ErbB3, ErbB3:PI3K, p-ErbB3:PI3K, ErbB3:Shc); ErbB4 (p-ErbB4, ErbB4:Shc); c-MET (p-c-MET, c-Met:HGF complex); AKT1 (p-AKT1); AKT2 (p-AKT2); AKT3 (p-AKT3); PTEN (p-PTEN); P70S6K (p-P70S6K); MEK (p-MEK); ERK1 (p-ERK1); ERK2 (p-ERK2); PDK1 (p-PDK1); PDK2 (p-PDK2); SGK3 (p-SGK3); 4E-BP1 (p-4E-BP1); PIK3R1 (p-PIK3R1); c-KIT (p-c-KIT); ER (p-ER); IGF-1R (p-IGF-1R, IGF-1R:IRS, IRS:PI3K, p-IRS, IGF-1R:PI3K); INSR (p-INSR); FLT3 (p-FLT3); HGFR1 (p-HGFR1); HGFR2 (p-HGFR2); RET (p-RET); PDGFRA (p-PDGFRA); PDGFRB (p-PDGFRB); VEGFR1 (p-VEGFR1, VEGFR1:PLCγ, VEGFR1:Src); VEGFR2 (p-VEGFR2, VEGFR2:PLCγ, VEGFR2:Src, VEGFR2:heparin sulphate, VEGFR2:VE-cadherin); VEGFR3 (p-VEGFR3); FGFR1 (p-FGFR1); FGFR2 (p-FGFR2); FGFR3 (p-FGFR3); FGFR4 (p-FGFR4); TIE1 (p-TIE1); TIE2 (p-TIE2); EPHA (p-EPHA); EPHB (p-EPHB); GSK-3P (p-GSK-3); NFKB (p-NFKB), IKB (p-IKB, p-P65:IKB); BAD (p-BAD, BAD: 14-3-3); mTOR (p-mTOR); Rsk-1 (p-Rsk-1); Jnk (p-Jnk); P38 (p-P38); STAT1 (p-STAT1); STAT3 (p-STAT3); FAK (p-FAK); RB (p-RB); Ki67; p53 (p-p53); CREB (p-CREB); c-Jun (p-c-Jun); c-Src (p-c-Src); paxillin (p-paxillin); GRB2 (p-GRB2), Shc (p-Shc), Ras (p-Ras), GAB1 (p-GAB1), SHP2 (p-SHP2), GRB2 (p-GRB2), CRKL (p-CRKL), PLCγ (p-PLCγ), PKC (e.g., p-PKCα, p-PKCPβ, p-PKCδ), adducin (p-adducin), RB1 (p-RB1), and PYK2 (p-PYK2).

As used herein, the term "dilution series" is intended to include a series of descending concentrations of a particular sample (e.g., cell lysate) or reagent (e.g., antibody). A dilution series is typically produced by a process of mixing a measured amount of a starting concentration of a sample or reagent with a diluent (e.g., dilution buffer) to create a lower concentration of the sample or reagent, and repeating the process enough times to obtain the desired number of serial dilutions. The sample or reagent can be serially diluted at least 2, 3, 4, 5, 6, 7, 8, 9, 10, 15, 20, 25, 30, 35, 40, 45, 50, 100, 500, or 1000-fold to produce a dilution series comprising at least 2, 3, 4, 5, 6, 7, 8, 9, 10, 11, 12, 13, 14, 15, 16, 17, 18, 19, 20, 25, 30, 35, 40, 45, or 50 descending concentrations of the sample or reagent. For example, a dilution series comprising a 2-fold serial dilution of a capture antibody reagent at a 1 mg/ml starting concentration can be produced by mixing an amount of the starting concentration of capture antibody with an equal amount of a dilution buffer to create a 0.5 mg/ml concentration of the capture antibody, and repeating the process to obtain capture antibody concentrations of 0.25 mg/ml, 0.125 mg/ml, 0.0625 mg/ml, 0.0325 mg/ml, etc.

The term "superior dynamic range" as used herein refers to the ability of an assay to detect a specific analyte in as few as one cell or in as many as thousands of cells. For example, the immunoassays described herein possess superior dynamic range because they advantageously detect a particular signal transduction molecule of interest in about 1-10,000 cells (e.g., about 1, 5, 10, 25, 50, 75, 100, 250, 500, 750, 1000, 2500, 5000, 7500, or 10,000 cells) using a dilution series of capture antibody concentrations.

The term "sample" as used herein includes any biological specimen obtained from a patient. Samples include, without limitation, whole blood, plasma, serum, red blood cells, white blood cells (e.g., peripheral blood mononuclear cells), ductal lavage fluid, nipple aspirate, lymph (e.g., disseminated tumor cells of the lymph node), bone marrow aspirate, saliva, urine, stool (i.e., feces), sputum, bronchial lavage fluid, tears, fine needle aspirate (e.g., harvested by random periareolar fine needle aspiration), any other bodily fluid, a tissue sample (e.g., tumor tissue) such as a biopsy of a tumor (e.g., needle biopsy) or a lymph node (e.g., sentinel lymph node biopsy), a tissue sample (e.g., tumor tissue) such as a surgical resection of a tumor, and cellular extracts thereof. In some embodiments, the sample is whole blood or a fractional component thereof such as plasma, serum, or a cell pellet. In certain instances, the sample is obtained by isolating circulating cells of a solid tumor from whole blood or a cellular fraction thereof using any technique known in the art. In other embodiments, the sample is a formalin fixed paraffin embedded (FFPE) tumor tissue sample, e.g., from a solid tumor of the breast.

A "biopsy" refers to the process of removing a tissue sample for diagnostic or prognostic evaluation, and to the tissue specimen itself. Any biopsy technique known in the art can be applied to the methods and compositions of the present invention. The biopsy technique applied will generally depend on the tissue type to be evaluated and the size and type of the tumor (i.e., solid or suspended (i.e., blood or ascites)), among other factors. Representative biopsy techniques include excisional biopsy, incisional biopsy, needle biopsy (e.g., core needle biopsy, fine-needle aspiration biopsy, etc.), surgical biopsy, and bone marrow biopsy. Biopsy techniques are discussed, for example, in *Harrison's Principles of Internal Medicine*, Kasper, et al., eds., 16th ed., 2005, Chapter 70, and throughout Part V. One skilled in the art will appreciate that biopsy techniques can be performed to identify cancerous and/or precancerous cells in a given tissue sample.

As used herein, the term "circulating cells" comprises extratumoral cells that have either metastasized or micro-metastasized from a solid tumor. Examples of circulating cells include, but are not limited to, circulating tumor cells, cancer stem cells, and/or cells that are migrating to the tumor (e.g., circulating endothelial progenitor cells, circulating endothelial cells, circulating pro-angiogenic myeloid cells, circulating dendritic cells, etc.). Patient samples containing circulating cells can be obtained from any accessible biological fluid (e.g., whole blood, serum, plasma, sputum, bronchial lavage fluid, urine, nipple aspirate, lymph, saliva, fine needle aspirate, etc.). In certain instances, the whole blood sample is separated into a plasma or serum fraction and a cellular fraction (i.e., cell pellet). The cellular fraction typically contains red blood cells, white blood cells, and/or circulating cells of a solid tumor such as circulating tumor cells (CTCs), circulating endothelial cells (CECs), circulating endothelial progenitor cells (CEPCs), cancer stem cells (CSCs), disseminated tumor cells of the lymph node, and combinations thereof. The plasma or serum fraction usually contains, inter alia, nucleic acids (e.g., DNA, RNA) and proteins that are released by circulating cells of a solid tumor.

Circulating cells are typically isolated from a patient sample using one or more separation methods including, for example, immunomagnetic separation (see, e.g., Racila et al., *Proc. Natl. Acad. Sci. USA*, 95:4589-4594 (1998); Bilkenroth et al., *Int. J. Cancer*, 92:577-582 (2001)), the CellTracks® System by Immunicon (Huntingdon Valley, Pa.), microfluidic separation (see, e.g., Mohamed et al., *IEEE Trans. Nanobiosci.*, 3:251-256 (2004); Lin et al., Abstract No. 5147, 97th AACR Annual Meeting, Washington, D.C. (2006)), FACS (see, e.g., Mancuso et al., *Blood*, 97:3658-3661 (2001)), density gradient centrifugation (see, e.g., Baker et al., *Clin. Cancer Res.*, 13:4865-4871 (2003)), and depletion methods (see, e.g., Meye et al., *Int. J. Oncol.*, 21:521-530 (2002)).

Signal transduction molecules of interest are typically extracted shortly after the circulating cells are isolated to preserve their in situ activation state, preferably within about 24, 6, or 1 hr, and more preferably within about 30, 15, or 5 minutes. The isolated cells may also be incubated with one or more growth factors, usually at nanomolar to micromolar concentrations, for about 1-30 minutes to resuscitate or stimulate activation of the signal transduction molecules (see, e.g., Irish et al., *Cell*, 118:217-228 (2004)). For example, to evaluate potential anticancer therapies for an individual patient, the isolated cells can be incubated with one or more anticancer drugs at varying doses. Growth factor stimulation can then be performed for a few minutes (e.g., about 1-5 minutes) or for several hours (e.g., about 1-6 hours). The differential activation of signaling pathways with and without anticancer drugs can aid in the selection of a suitable cancer therapy at the proper dose for each individual patent. Circulating cells can also be isolated from a patient sample during anticancer drug treatment and stimulated with one or more growth factors to determine whether a change in therapy should be implemented.

The term "subject" or "patient" or "individual" typically includes humans, but can also include other animals such as, e.g., other primates, rodents, canines, felines, equines, ovines, porcines, and the like.

An "array" or "microarray" comprises a distinct set and/or dilution series of capture antibodies immobilized or restrained on a solid support such as, for example, glass (e.g., a glass slide), plastic, chips, pins, filters, beads (e.g., magnetic beads, polystyrene beads, etc.), paper, membrane (e.g., nylon, nitrocellulose, polyvinylidene fluoride (PVDF), etc.), fiber bundles, or any other suitable substrate. The capture antibodies are generally immobilized or restrained on the solid support via covalent or noncovalent interactions (e.g., ionic bonds, hydrophobic interactions, hydrogen bonds, Van der Waals forces, dipole-dipole bonds). In certain instances, the capture antibodies comprise capture tags which interact with capture agents bound to the solid support. The arrays used in the assays described herein typically comprise a plurality of different capture antibodies and/or capture antibody concentrations that are coupled to the surface of a solid support in different known/addressable locations.

The term "capture antibody" is intended to include an immobilized antibody which is specific for (i.e., binds, is bound by, or forms a complex with) one or more analytes of interest in a sample such as a cellular extract. In particular embodiments, the capture antibody is restrained on a solid support in an array. Suitable capture antibodies for immobilizing any of a variety of signal transduction molecules on a solid support are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.).

The term "detection antibody" as used herein includes an antibody comprising a detectable label which is specific for (i.e., binds, is bound by, or forms a complex with) one or more analytes of interest in a sample. The term also encompasses an antibody which is specific for one or more analytes of interest, wherein the antibody can be bound by another species that comprises a detectable label. Examples of detectable labels include, but are not limited to, biotin/streptavidin labels, nucleic acid (e.g., oligonucleotide) labels, chemically reactive labels, fluorescent labels, enzyme labels, radioactive labels, and combinations thereof. Suitable detection antibodies for detecting the activation state and/or total amount of any of a variety of signal transduction molecules are available from Upstate (Temecula, Calif.), Biosource (Camarillo, Calif.), Cell Signaling Technologies (Danvers, Mass.), R&D Systems (Minneapolis, Minn.), Lab Vision (Fremont, Calif.), Santa Cruz Biotechnology (Santa Cruz, Calif.), Sigma (St. Louis, Mo.), and BD Biosciences (San Jose, Calif.). As a non-limiting example, phospho-specific antibodies against various phosphorylated forms of signal transduction molecules such as EGFR, c-KIT, c-Src, FLK-1, PDGFRA, PDGFRB, AKT, MAPK, PTEN, Raf, and MEK are available from Santa Cruz Biotechnology.

The term "activation state-dependent antibody" includes a detection antibody which is specific for (i.e., binds, is bound by, or forms a complex with) a particular activation state of one or more analytes of interest in a sample. In preferred embodiments, the activation state-dependent antibody detects the phosphorylation, ubiquitination, and/or complexation state of one or more analytes such as one or more signal transduction molecules. In some embodiments, the phosphorylation of members of the EGFR family of receptor tyrosine kinases and/or the formation of heterodimeric complexes between EGFR family members is detected using activation state-dependent antibodies. In particular embodiments, activation state-dependent antibodies are useful for detecting one or more sites of phosphorylation in one or more of the following signal transduction molecules (phosphorylation sites correspond to the position of the amino acid in the human protein sequence): EGFR/HER1/ErbB1 (e.g., tyrosine (Y) 1068); ErbB2/HER2 (e.g., Y1248); ErbB3/HER3 (e.g., Y1289); ErbB4/HER4 (e.g., Y1284); c-Met (e.g., Y1003, Y1230, Y1234, Y1235, and/or Y1349); SGK3 (e.g., threonine (T) 256 and/or serine (S) 422); 4E-BP1 (e.g., T70); ERK1 (e.g., T185, Y187, T202, and/or Y204); ERK2 (e.g., T185, Y187, T202, and/or Y204); MEK (e.g., S217 and/or S221); PIK3R1 (e.g., Y688); PDK1 (e.g., S241); P70S6K (e.g., T229, T389, and/or S421); PTEN (e.g., S380); AKT1 (e.g., S473 and/or T308); AKT2 (e.g., S474 and/or T309); AKT3 (e.g., S472 and/or T305); GSK-3β (e.g., S9); NFKB (e.g., S536); IKB (e.g., S32); BAD (e.g., S112 and/or S136); mTOR (e.g., S2448); Rsk-1 (e.g., T357 and/or S363); Jnk (e.g., T183 and/or Y185); P38 (e.g., T180 and/or Y182); STAT3 (e.g., Y705 and/or S727); FAK (e.g., Y397, Y576, S722, Y861, and/or S910); RB (e.g., S249, T252, S612, and/or S780); RB1 (e.g., S780); adducin (e.g., S662 and/or S724); PYK2 (e.g., Y402 and/or Y881); PKCα (e.g., S657); PKCα/β (e.g., T368 and/or T641); PKCδ (e.g., T505); p53 (e.g., S392 and/or S20); CREB (e.g., S133); c-Jun (e.g., S63); c-Src (e.g., Y416); and paxillin (e.g., Y31 and/or Y118).

The term "activation state-independent antibody" includes a detection antibody which is specific for (i.e., binds, is bound by, or forms a complex with) one or more analytes of interest in a sample irrespective of their activation state. For example, the activation state-independent antibody can detect both phosphorylated and unphosphorylated forms of one or more analytes such as one or more signal transduction molecules.

The term "nucleic acid" or "polynucleotide" includes deoxyribonucleotides or ribonucleotides and polymers thereof in either single- or double-stranded form such as, for example, DNA and RNA. Nucleic acids include nucleic acids containing known nucleotide analogs or modified backbone residues or linkages, which are synthetic, naturally occurring, and non-naturally occurring, and which have similar binding properties as the reference nucleic acid.

Examples of such analogs include, without limitation, phosphorothioates, phosphoramidates, methyl phosphonates, chiral-methyl phosphonates, 2'-O-methyl ribonucleotides, and peptide-nucleic acids (PNAs). Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof and complementary sequences as well as the sequence explicitly indicated.

The term "oligonucleotide" includes a single-stranded oligomer or polymer of RNA, DNA, RNA/DNA hybrid, and/or a mimetic thereof. In certain instances, oligonucleotides are composed of naturally-occurring (i.e., unmodified) nucleobases, sugars, and internucleoside (backbone) linkages. In certain other instances, oligonucleotides comprise modified nucleobases, sugars, and/or internucleoside linkages.

As used herein, the term "mismatch motif" or "mismatch region" refers to a portion of an oligonucleotide that does not have 100% complementarity to its complementary sequence. An oligonucleotide may have at least one, two, three, four, five, six, or more mismatch regions. The mismatch regions may be contiguous or may be separated by 1, 2, 3, 4, 5, 6, 7, 8, 9, 10, 11, 12, or more nucleotides. The mismatch motifs or regions may comprise a single nucleotide or may comprise two, three, four, five, or more nucleotides.

The phrase "stringent hybridization conditions" refers to conditions under which an oligonucleotide will hybridize to its complementary sequence, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization.

The terms "substantially identical" or "substantial identity," in the context of two or more nucleic acids, refer to two or more sequences or subsequences that are the same or have a specified percentage of nucleotides that are the same (i.e., at least about 60%, preferably at least about 65%, 70%, 75%, 80%, 85%, 90%, or 95% identity over a specified region) when compared and aligned for maximum correspondence over a comparison window or designated region as measured using a sequence comparison algorithm or by manual alignment and visual inspection. This definition, when the context indicates, also refers analogously to the complement of a sequence. Preferably, the substantial identity exists over a region that is at least about 5, 10, 15, 20, 25, 30, 35, 40, 45, 50, 75, or 100 nucleotides in length.

The term "incubating" is used synonymously with "contacting" and "exposing" and does not imply any specific time or temperature requirements unless otherwise indicated.

"Receptor tyrosine kinases" or "RTKs" include a family of fifty-six (56) proteins characterized by a transmembrane domain and a tyrosine kinase motif. RTKs function in cell signaling and transmit signals regulating growth, differentiation, adhesion, migration, and apoptosis. The mutational activation and/or overexpression of receptor tyrosine kinases transforms cells and often plays a crucial role in the development of cancers. RTKs have become targets of various molecularly targeted agents such as trastuzumab, cetuximab, gefitinib, erlotinib, sunitinib, imatinib, nilotinib, and the like. One well-characterized signal transduction pathway is the MAP kinase pathway, which is responsible for transducing the signal from epidermal growth factor (EGF) to the promotion of cell proliferation in cells.

The term "progression free survival" or "PFS" includes the length of time during and after a treatment of a disease (e.g., cancer) in which a patient is living with the disease without additional symptoms of the disease.

The term "triple-negative" in the context of the present invention includes a tumor cell (e.g., a circulating tumor cell), a tumor, or a cancer such as triple-negative metastatic breast cancer (TNMBC) in which there is no detectable expression of estrogen receptor (ER), progesterone receptor (PR), or human epidermal growth factor receptor 2 (HER2).

III. Description of the Embodiments

The present invention provides methods for detecting the status (e.g., expression and/or activation levels) of components of signal transduction pathways in tumor cells derived from tumor tissue or circulating cells of a solid tumor with an assay such as a specific, multiplex, high-throughput proximity assay as described herein. The present invention also provides methods for selecting appropriate therapies to downregulate one or more deregulated signal transduction pathways. Thus, certain embodiments of the invention may be used to facilitate the design of personalized therapies based on the particular molecular signature provided by the collection of total and/or activated signal transduction proteins in a given patient's tumor (e.g., a triple-negative breast tumor).

In particular aspects, the present invention provides molecular markers (biomarkers) that enable the determination or prediction of whether a particular cancer can respond or is likely to respond favorably to one or more anticancer drugs such as, e.g., a combination of bevacizumab (Avastin®), carboplatin, and paclitaxel (e.g., Abraxane® or nabP) ("triplet therapy"). In specific embodiments, measuring the level of expression and/or activation of at least one, two, or more (e.g., all) of VEGFR2, c-KIT, HER1, and/or IGF-1R is particularly useful for selecting a suitable anticancer drug and/or identifying or predicting efficacy or a response thereto in cells such as triple-negative tumor cells.

In one aspect, the present invention provides a method for determining the sensitivity of a triple-negative tumor cell to therapy with an anticancer drug, the method comprising:
(a) lysing the tumor cell to produce a cellular extract;
(b) determining the expression level of one or more analytes selected from the group consisting of VEGFR2, c-KIT, HER1, and/or IGF-1R in the cellular extract; and
(c) comparing the expression level of VEGFR2, c-KIT, HER1, and/or IGF-1R in the cellular extract determined in step (b) to a reference expression level of VEGFR2, c-KIT, HER1, and/or IGF-1R,
wherein the presence of a low level of VEGFR2 expression, a low level of c-KIT expression, a high level of HER1 expression, and/or a low level of IGF-1R expression in the cellular extract compared to the reference expression level indicates that the tumor cell is sensitive to the anticancer drug.

In some embodiments, the presence of a medium to high level of VEGFR2 expression, a medium to high level of c-KIT expression, a low to medium level of HER1 expression, and/or a medium to high level of IGF-1R expression in the cellular extract compared to the reference expression level indicates that the tumor cell is resistant to the anticancer drug. In one particular embodiment, the method comprises determining the expression level of a combination of analytes comprising, consisting essentially of, or consisting of VEGFR2 and c-KIT in the cellular extract. In another particular embodiment, the method comprises determining the expression level of a combination of analytes comprising, consisting essentially of, or consisting of VEGFR2 and HER1 in the cellular extract. In yet another particular embodiment, the method comprises determining the expression level of a combination of analytes comprising, consisting essentially of, or consisting of VEGFR2, c-KIT, and HER1 in the cellular extract. In a further particular embodiment, the method comprises determining the expression level of a combination of analytes comprising, consisting essentially of, or consisting of VEGFR2, c-KIT, HER1, and IGF-1R in the cellular extract. In certain instances, the method of the present invention further comprises determining the activation level of at least one, two, or more (e.g., all) of VEGFR2, c-KIT, HER1, IGF-1R, and/or AKT in the cellular extract. In other instances, the method further comprises contacting the tumor cell with the anticancer drug prior to step (a).

In other embodiments, the tumor cell is a breast cancer cell. In certain instances, the tumor cell is a fine needle aspirate (FNA) cell obtained from a tumor such as a triple-negative breast tumor or a circulating tumor cell (CTC) obtained from a bodily fluid sample. The tumor cell is typically isolated from a sample including whole blood, serum, plasma, or tumor tissue. In particular embodiments, the sample is obtained from a subject with triple-negative metastatic breast cancer (TNMBC).

In another aspect, the present invention provides a method for predicting the response of a triple-negative breast tumor to therapy with an anticancer drug, the method comprising:
(a) lysing a tumor cell obtained from the triple-negative breast tumor to produce a cellular extract;
(b) determining the expression level of VEGFR2, c-KIT, HER1, and/or IGF-1R in the cellular extract; and
(c) comparing the expression level of VEGFR2, c-KIT, HER1, and/or IGF-1R in the cellular extract determined in step (b) to a reference expression level of VEGFR2, c-KIT, HER1, and/or IGF-1R,
wherein the presence of a low level of VEGFR2 expression, a low level of c-KIT expression, a high level of HER1 expression, and/or a low level of IGF-1R expression in the cellular extract compared to the reference expression level is predictive of response to therapy with the anticancer drug.

In some embodiments, the presence of a medium to high level of VEGFR2 expression, a medium to high level of c-KIT expression, a low to medium level of HER1 expression, and/or a medium to high level of IGF-1R expression in the cellular extract is predictive of a lack of response to therapy with the anticancer drug. In one particular embodiment, the method comprises determining the expression level of a combination of analytes comprising, consisting essentially of, or consisting of VEGFR2 and c-KIT in the cellular extract. In another particular embodiment, the method comprises determining the expression level of a combination of analytes comprising, consisting essentially of, or consisting of VEGFR2 and HER1 in the cellular extract. In yet another particular embodiment, the method comprises determining the expression level of a combination of analytes comprising, consisting essentially of, or consisting of VEGFR2, c-KIT, and HER1 in the cellular extract. In a further particular embodiment, the method comprises determining the expression level of a combination of analytes comprising, consisting essentially of, or consisting of VEGFR2, c-KIT, HER1, and IGF-1R in the cellular extract. In certain instances, the method of the present invention further comprises determining the activation level of at least one, two, or more (e.g., all) of VEGFR2, c-KIT, HER1, IGF-1R, and/or AKT in the cellular extract. In other instances, the method further comprises incubating the tumor cell obtained from the triple-negative breast tumor with the anticancer drug prior to step (a).

In other embodiments, the tumor cell is a fine needle aspirate (FNA) cell obtained from a tumor such as a triple-negative breast tumor or a circulating tumor cell (CTC) obtained from a bodily fluid sample. The tumor cell is typically isolated from a sample including whole blood, serum, plasma, or tumor tissue. In particular embodiments, the sample is obtained from a subject with triple-negative metastatic breast cancer (TNMBC).

In some instances, the presence of a low level of VEGFR2 expression is predictive of a longer duration of progression free survival (PFS). In other instances, the presence of a low level of c-KIT expression is predictive of a longer duration of PFS. In further instances, the presence of a high level of HER1 expression is predictive of a longer duration of PFS. In yet other instances, the presence of a low level of IGF-1R expression is predictive of a longer duration of PFS. In particular instances, the presence of a low level of VEGFR2 expression in combination with the presence of a low level of c-KIT expression and/or a high level of HER1 expression is predictive of a longer duration of PFS compared to the expression level of VEGFR2, c-KIT, or HER1 alone.

In certain embodiments, the methods of the present invention (e.g., methods for determining the sensitivity of a triple-negative tumor cell to therapy with an anticancer drug and for predicting the response of a triple-negative breast tumor to therapy with an anticancer drug) may further comprise step (d) of providing the result of the comparison obtained in step (c) to a user (e.g., a clinician such as an oncologist or a general practitioner) in a readable format. In certain embodiments, the methods of the present invention may further comprise sending or reporting the result of the comparison obtained in step (c) to a clinician, e.g., an oncologist or a general practitioner. In other instances, the methods of the present invention may further comprise recording or storing the result of the comparison obtained in step (c) in a computer database or other suitable machine or device for storing information, e.g., at a laboratory.

In particular embodiments, the expression level of VEGFR2, c-KIT, HER1, and/or IGF-1R is determined by detecting total protein levels of VEGFR2, c-KIT, HER1, and/or IGF-1R, e.g., using an immunoassay with analyte-specific antibodies. Total expression level and/or status can be determined using any of a variety of techniques. As non-limiting examples, the expression level of VEGFR2, c-KIT, HER1, and/or IGF-1R can be determined with a single detection assay or with a proximity dual detection assay as described herein. In preferred embodiments, the proximity dual detection assay is a Collaborative Enzyme Enhanced Reactive ImmunoAssay (CEER).

In some embodiments, the expression (e.g., total) level and/or activation (e.g., phosphorylation) level of the one or more analytes is expressed as a relative fluorescence unit (RFU) value that corresponds to the signal intensity for a particular analyte of interest that is determined using, e.g., CEER. In other embodiments, the expression level and/or activation level of the one or more analytes is quantitated by calibrating or normalizing the RFU value that is determined using, e.g., a proximity assay such as CEER, against a standard curve generated for the particular analyte of interest. In certain instances, the RFU value can be calculated based upon a standard curve.

In further embodiments, the expression level and/or activation level of the one or more analytes is expressed as "low", "medium", or "high" that corresponds to increasing signal intensity for a particular analyte of interest that is determined using, e.g., a proximity assay such as CEER. In some instances, an undetectable or minimally detectable level of expression or activation of a particular analyte of interest that is determined using, e.g., a proximity assay such as CEER, may be expressed as "undetectable". In other instances, a low level of expression or activation of a particular analyte of interest that is determined using, e.g., a proximity assay such as CEER, may be expressed as "low". In yet other instances, a moderate level of expression or activation of a particular analyte of interest that is determined using, e.g., a proximity assay such as CEER, may be expressed as "medium". In still yet other instances, a moderate to high level of expression or activation of a particular analyte of interest that is determined using, e.g., a proximity assay such as CEER, may be expressed as "medium to high". In further instances, a very high level of expression or activation of a particular analyte of interest that is determined using, e.g., a proximity assay such as CEER, may be expressed as "high".

In particular embodiments, the reference expression level and/or activation level of a particular analyte of interest is calculated from one or more standard curves generated from a sample such as, for example, a cancer cell line. As a non-limiting example, for each assay used to determine the expression level or activation level of a particular analyte of interest, a sigmoidal standard curve can be generated from one or multiple (e.g., two, three, four, five, six, seven, etc.) concentrations of serially diluted cell lysates prepared from a cancer cell line. In preferred embodiments, the cancer cell line expresses one or more analytes of interest, e.g., VEGFR2, c-KIT, HER1, and/or IGF-1R. Each curve can be plotted as a function of signal intensity vs. log concentration derived units, and CU (Computed Unit) can be calculated based on the standard curve. Example 7 provides a more detailed description of the quantitation of the expression and/or activation levels of a particular analyte of interest against a standard curve generated for the particular analyte of interest.

In certain embodiments, the expression level or activation level of a particular analyte of interest, when expressed as "low", "medium", or "high", may correspond to a level of expression or activation that is at least about 0; 5,000; 10,000; 15,000; 20;000; 25,000; 30,000; 35,000; 40,000; 45,000; 50,000; 60,000; 70;000; 80,000; 90,000; 100,000 RFU; or more, e.g., when compared to a reference expression level and/or activation level for that particular analyte of interest in a negative control (e.g., an IgG control), in a standard curve generated for the analyte of interest (e.g., a standard curve generated from a cancer cell line), in a positive control such as a pan-CK control, in the presence of an anticancer drug, and/or in the absence of an anticancer drug. In some instances, the correlation is analyte-specific. As a non-limiting example, a "low" level of expression or activation determined using, e.g., a proximity assay such as CEER, may correspond 10,000 RFUs in expression or activation for one analyte and 50,000 RFUs for another analyte when compared to a reference expression or activation level.

In certain embodiments, the expression or activation level of a particular analyte of interest may correspond to a level of expression or activation referred to as "low", "medium" or "high" that is relative to a reference expression level or activation level for that particular analyte of interest, e.g., when compared to a negative control such as an IgG control, when compared to a standard curve generated for the analyte of interest (e.g., a standard curve generated from a cancer cell line), when compared to a positive control such as a pan-CK control, when compared to an expression or activation level determined in the presence of an anticancer drug, and/or when compared to an expression or activation level determined in the absence of an anticancer drug. In some instances, the correlation is analyte-specific. As a non-limiting example, a "low" level of expression or activation determined using, e.g., a proximity assay such as CEER, may correspond to a 2-fold increase in expression or activation for one analyte and a 5-fold increase for another analyte when compared to a reference expression or activation level.

In certain embodiments, the expression or activation level of a particular analyte of interest may correspond to a level of expression or activation that is compared to a reference expression level and/or activation level for that particular analyte of interest in a negative control (e.g., an IgG control), in a standard curve generated for the analyte of interest (e.g., a standard curve generated from a cancer cell line), in a positive control such as a pan-CK control, in the presence of an anticancer drug, and/or in the absence of an anticancer drug.

In certain embodiments, a higher level of expression or activation of a particular analyte of interest is considered to be present in a sample (e.g., a cellular extract) when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold higher (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold higher) than the reference expression or activation level for that particular analyte of interest in a negative control (e.g., an IgG control), in a standard curve generated for the analyte of interest (e.g., a standard curve generated from a cancer cell line), in a positive control (e.g., a pan-CK control), in the presence of an anticancer drug, and/or in the absence of an anticancer drug.

In other embodiments, a lower level of expression or activation of a particular analyte of interest is considered to be present in a sample (e.g., a cellular extract) when the expression or activation level is at least about 1.5, 2, 2.5, 3, 3.5, 4, 4.5, 5, 5.5, 6, 6.5, 7, 7.5, 8, 8.5, 9, 9.5, 10, 15, 20, 25, 30, 35, 40, 45, 50, or 100-fold lower (e.g., about 1.5-3, 2-3, 2-4, 2-5, 2-10, 2-20, 2-50, 3-5, 3-10, 3-20, 3-50, 4-5, 4-10, 4-20, 4-50, 5-10, 5-15, 5-20, or 5-50-fold lower) than the reference expression or activation level for that particular analyte of interest in a negative control (e.g., an IgG control), in a standard curve generated for the analyte of interest (e.g., a standard curve generated from a cancer cell line), in a positive control (e.g., a pan-CK control), in the presence of an anticancer drug, and/or in the absence of an anticancer drug.

In further embodiments, the reference expression or activation level of a particular analyte of interest is a cutoff value. In some instances, the cutoff value includes a number chosen on the basis of population analysis of a particular analyte of interest that is used for comparison to the expression or activation level of that analyte in the cellular extract. As a non-limiting example, a cutoff value can be derived by dividing the expression or activation level of a particular analyte of interest from a population of individuals into "high" and "low" groups and selected to be at or close to the median expression or activation level of that analyte in the population. The expression or activation level of the analyte of interest in the cellular extract can be compared to the cutoff value and determined to be a "high" and "low" level of expression or activation based on whether the expression or activation level of the analyte in the cellular extract is above (e.g., "high") or below (e.g., "low") the cutoff value. Example 5 provides one exemplary embodiment of calculating, selecting, and using cutoff values in accordance with the methods of the present invention. In other embodiments, the cutoff value can be derived from a standard curve generated for a particular analyte of interest (e.g., a standard curve generated from a cancer cell line) and compared to the expression or activation level of that analyte in the cellular extract. Those of skill in the art will recognize that a cutoff value can be determined according to the needs of the user and characteristics of the analyzed population.

In some embodiments, the anticancer drug comprises one or more agents that interfere with the function of abnormally expressed and/or activated signal transduction pathway components in cancer cells. Non-limiting examples of such agents include those listed below in Table 1 of PCT Publication No. WO 2010/132723, the disclosure of which is herein incorporated by reference in its entirety for all purposes.

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the isolated cells are treated with one or more anti-signaling agents, anti-proliferative agents, and/or hormonal therapeutic agents in combination with at least one chemotherapeutic agent.

Examples of anti-signaling agents suitable for use in the present invention include, without limitation, monoclonal antibodies such as trastuzumab (Herceptin®), pertuzumab (2C4), alemtuzumab (Campath®), bevacizumab (Avastin®), cetuximab (Erbitux®), gemtuzumab (Mylotarg®), panitumumab (Vectibix™), rituximab (Rituxan®), and tositumomab (BEXXAR®); tyrosine kinase inhibitors such as gefitinib (Iressa®), sunitinib (Sutent®), erlotinib (Tarceva®), lapatinib (GW-572016; Tykerb®), canertinib (CI 1033), semaxinib (SU5416), vatalanib (PTK787/ZK222584), sorafenib (BAY 43-9006; Nexavar®), imatinib mesylate (Gleevec®), leflunomide (SU101), vandetanib (ZACTIMA™; ZD6474), pelitinib, CP-654577, CP-724714, HKI-272, PKI-166, AEE788, BMS-599626, HKI-357, BIBW 2992, ARRY-334543, JNJ-26483327, and JNJ-26483327; and combinations thereof.

Exemplary anti-proliferative agents include mTOR inhibitors such as sirolimus (rapamycin), temsirolimus (CCI-779), everolimus (RAD001), BEZ235, and XL765; AKT inhibitors such as 1 L6-hydroxymethyl-chiro-inositol-2-(R)-2-O-methyl-3-O-octadecyl-sn-glycerocarbonate, 9-methoxy-2-methylellipticinium acetate, 1,3-dihydro-1-(1-((4-(6-phenyl-1H-imidazo[4,5-g]quinoxalin-7-yl)phenyl) methyl)-4-piperidinyl)-2H-benzimidazol-2-one, 10-(4'-(N-diethylamino)butyl)-2-chlorophenoxazine, 3-formylchromone thiosemicarbazone (Cu(II)C2 complex), API-2, a 15-mer peptide derived from amino acids 10-24 of the proto-oncogene TCL1 (Hiromura et al., *J. Biol. Chem.*, 279:53407-53418 (2004), KP372-1, and the compounds described in Kozikowski et al., *J. Am. Chem. Soc.*, 125: 1144-1145 (2003) and Kau et al., *Cancer Cell*, 4:463-476 (2003); PI3K inhibitors such as PX-866, wortmannin, LY 294002, quercetin, tetrodotoxin citrate, thioperamide maleate, GDC-0941 (957054-30-7), IC87114, PI-103, PIK93, BEZ235 (NVP-BEZ235), TGX-115, ZSTK474, (−)-deguelin, NU 7026, myricetin, tandutinib, GDC-0941 bismesylate, GSK690693, KU-55933, MK-2206, OSU-03012, perifosine, triciribine, XL-147, PIK75, TGX-221, NU 7441, PI 828, XL-765, and WHI-P 154; MEK inhibitors such as PD98059, ARRY-162, RDEA119, U0126, GDC-0973, PD184161, AZD6244, AZD8330, PD0325901, and ARRY-142886; and combinations thereof.

Non-limiting examples of pan-HER inhibitors include PF-00299804, neratinib (HKI-272), AC480 (BMS-599626), BMS-690154, PF-02341066, HM781-36B, CI-1033, BIBW-2992, and combinations thereof.

Non-limiting examples of chemotherapeutic agents include platinum-based drugs (e.g., oxaliplatin, cisplatin, carboplatin, spiroplatin, iproplatin, satraplatin, etc.), alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, 6-mercaptopurine, methotrexate, leucovorin, capecitabine, cytarabine, floxuridine, fludarabine, gemcitabine (Gemzar®), pemetrexed (ALIMTA®), raltitrexed, etc.), plant alkaloids (e.g., vincristine, vinblastine, vinorelbine, vindesine, podophyllotoxin, paclitaxel (Taxol®), docetaxel (Taxotere®), etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), pharmaceutically acceptable salts thereof, stereoisomers thereof, derivatives thereof, analogs thereof, and combinations thereof.

Examples of hormonal therapeutic agents include, without limitation, aromatase inhibitors (e.g., aminoglutethimide, anastrozole (Arimidex®), letrozole (Femara®), vorozole, exemestane (Aromasin®), 4-androstene-3,6,17-trione (6-OXO), 1,4,6-androstatrien-3,17-dione (ATD), formestane (Lentaron®), etc.), selective estrogen receptor modulators (e.g., bazedoxifene, clomifene, fulvestrant, lasofoxifene, raloxifene, tamoxifen, toremifene, etc.), steroids (e.g., dexamethasone), finasteride, and gonadotropin-releasing hormone agonists (GnRH) such as goserelin, pharmaceutically acceptable salts thereof, stereoisomers thereof, derivatives thereof, analogs thereof, and combinations thereof.

Non-limiting examples of cancer vaccines useful in the present invention include ANYARA from Active Biotech, DCVax-LB from Northwest Biotherapeutics, EP-2101 from IDM Pharma, GV1001 from Pharmexa, 10-2055 from Idera Pharmaceuticals, INGN 225 from Introgen Therapeutics and Stimuvax from Biomira/Merck.

Examples of radiotherapeutic agents include, but are not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

In preferred embodiments, the anticancer drug is a combination of bevacizumab (Avastin®), carboplatin, and paclitaxel ("triplet therapy"). In some instances, the paclitaxel is a nanoparticle albumin-bound (nab) paclitaxel (Abraxane® or nabP). In other embodiments, the anticancer drug comprises one or more of the following: bevacizumab (Avastin®), carboplatin, paclitaxel (e.g., nabP), iniparib (BSI 201; 4-iodo-3-nitrobenzamide), NK012 (an SN-38-releasing nanodevice constructed by covalently attaching SN-38 to the block copolymer PEG-PGlu, followed by self-assembly of amphiphilic block copolymers in aqueous media), glembatumumab vedotin, (also known as CDX-011 or CR011-vcMMAE; human monoclonal antibody glembatumumab (CR011) linked to monomethyl auristatin E (MMAE) that targets cancer cells expressing transmembrane glycoprotein NMB), or combinations thereof. In one particular embodiment, the anticancer drug is a combination of iniparib (a PARP inhibitor), gemcitabine (Gemzar®), and carboplatin.

In some embodiments, the methods further comprise determining the expression and/or activation level of one or more additional signal transduction molecules in the cellular extract. Non-limiting examples of additional signal transduction molecules that can be interrogated for expression (e.g., total amount) levels and/or activation (e.g., phosphorylation) levels in a sample such as a cellular extract include receptor tyrosine kinases, non-receptor tyrosine kinases, tyrosine kinase signaling cascade components, nuclear hormone receptors, nuclear receptor coactivators, nuclear receptor repressors, and combinations thereof. Specific examples of signal transduction molecules and pathways that may be interrogated using the present invention include those shown in Table 2 of PCT Publication No. WO 2010/132723, the disclosure of which is herein incorporated by reference in its entirety for all purposes. In particular embodiments, the one or more additional signal transduction molecules is selected from the group consisting of HER2, p95HER2, HER3, HER4, PI3K, AKT, MEK, PTEN, SGK3, 4E-BP1, ERK2 (MAPK1), ERK1 (MAPK3), PDK1, P70S6K, GSK-3P, Shc, c-MET, VEGFR1, VEGFR3, a receptor dimer, and combinations thereof.

In certain embodiments, the present invention further comprises determining the expression (e.g., total) level and/or activation (e.g., phosphorylation) level of one or more (e.g., at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more) additional analytes in the cellular extract. In some embodiments, the one or more (e.g., at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more) additional analytes comprises one or more signal transduction molecules selected from the group consisting of receptor tyrosine kinases, non-receptor tyrosine kinases, tyrosine kinase signaling cascade components, nuclear hormone receptors, nuclear receptor coactivators, nuclear receptor repressors, and combinations thereof.

In particular embodiments, the present invention further comprises determining the expression (e.g., total) level and/or activation (e.g., phosphorylation) level of one or any combination of 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or more of the following additional analytes in a cellular extract: HER2, p95HER2, HER3, HER4, PI3K, AKT, MEK, PTEN, SGK3, 4E-BP1, ERK2 (MAPK1), ERK1 (MAPK3), PDK1, P70S6K, GSK-3β, Shc, c-MET, VEGFR1, VEGFR3, PDK2, Raf, SRC, NFkB-1kB, mTOR, EPH-A, EPH-B, EPH-C, EPH-D, FLT-3, TIE-1, TIE-2, c-FMS, Abl, FTL 3, RET, FGFR1, FGFR2, FGFR3, FGFR4, ER, PR, NCOR, AIB1, RON, PIP2, PIP3, p27, protein tyrosine phosphatases (e.g., PTP1B, PTPN13, BDP1, etc.), receptor dimers, and combinations thereof.

IV. Construction of Antibody Arrays

In certain aspects, the expression level and/or activation state of one or more (e.g., a plurality) of analytes (e.g., signal transduction molecules) in a cellular extract of tumor cells such as breast cancer cells is detected using an antibody-based array comprising a dilution series of capture antibodies restrained on a solid support. The arrays typically comprise a plurality of different capture antibodies at a range of capture antibody concentrations that are coupled to the surface of the solid support in different addressable locations. In one embodiment, the array comprises capture antibodies for detecting and/or quantifying the expression and/or activation of at least one or more of VEGFR2, c-KIT, HER1, and/or IGF-1R and one or more controls such as, e.g., a negative control (e.g., an IgG control), a standard curve generated for the analyte of interest, and/or a positive control (e.g., a pan-CK control).

In one particular embodiment, the present invention provides an addressable array having superior dynamic range comprising a plurality of dilution series of capture antibodies restrained on a solid support, in which the capture antibodies in each dilution series are specific for one or more analytes corresponding to a component of a signal transduction pathway and other target proteins. In various aspects, this embodiment includes arrays that comprise components of signal transduction pathways characteristic of particular tumors, e.g., signal transduction pathways active in breast cancer cells. Thus, the present invention may be advantageously practiced wherein each signal transduction molecule or other protein of interest with a potential expression or activation defect causing breast cancer is represented on a single array or chip. In some aspects, the components of a given signal transduction pathway active in a particular tumor cell are arrayed in a linear sequence that corresponds to the sequence in which information is relayed through a signal transduction pathway within a cell. Examples of such arrays are described herein and also shown in FIGS. 5-9 of PCT Publication No. WO2009/108637, the disclosure of which is herein incorporated by reference in its entirety for all purposes. The capture antibodies specific for one or more components of a given signal transduction pathway active in a particular tumor cell can also be printed in a randomized fashion to minimize any surface-related artifacts.

The solid support can comprise any suitable substrate for immobilizing proteins. Examples of solid supports include, but are not limited to, glass (e.g., a glass slide), plastic, chips, pins, filters, beads, paper, membranes, fiber bundles, gels, metal, ceramics, and the like. Membranes such nylon (Biotrans™, ICN Biomedicals, Inc. (Costa Mesa, Calif.); Zeta-Probe®, Bio-Rad Laboratories (Hercules, Calif.)), nitrocellulose (Protran®, Whatman Inc. (Florham Park, N.J.)), and PVDF (Immobilon™, Millipore Corp. (Billerica, Mass.)) are suitable for use as solid supports in the arrays of the present invention. Preferably, the capture antibodies are restrained on glass slides coated with a nitrocellulose polymer, e.g., FAST® Slides, which are commercially available from Whatman Inc. (Florham Park, N.J.).

Particular aspects of the solid support which are desirable include the ability to bind large amounts of capture antibodies and the ability to bind capture antibodies with minimal denaturation. Another suitable aspect is that the solid support displays minimal "wicking" when antibody solutions containing capture antibodies are applied to the support. A solid support with minimal wicking allows small aliquots of capture antibody solution applied to the support to result in small, defined spots of immobilized capture antibody.

The capture antibodies are typically directly or indirectly (e.g., via capture tags) restrained on the solid support via covalent or noncovalent interactions (e.g., ionic bonds, hydrophobic interactions, hydrogen bonds, Van der Waals forces, dipole-dipole bonds). In some embodiments, the capture antibodies are covalently attached to the solid support using a homobifunctional or heterobifunctional crosslinker using standard crosslinking methods and conditions. Suitable crosslinkers are commercially available from vendors such as, e.g., Pierce Biotechnology (Rockford, Ill.).

Methods for generating arrays suitable for use in the present invention include, but are not limited to, any technique used to construct protein or nucleic acid arrays. In some embodiments, the capture antibodies are spotted onto an array using a microspotter, which are typically robotic printers equipped with split pins, blunt pins, or ink jet printing. Suitable robotic systems for printing the antibody arrays described herein include the PixSys 5000 robot (Cartesian Technologies; Irvine, Calif.) with ChipMaker2 split pins (TeleChem International; Sunnyvale, Calif.) as well as other robotic printers available from BioRobics (Woburn, Mass.) and Packard Instrument Co. (Meriden, Conn.). Preferably, at least 2, 3, 4, 5, or 6 replicates of each capture antibody dilution are spotted onto the array.

Another method for generating arrays suitable for use in the present invention comprises dispensing a known volume of a capture antibody dilution at each selected array position by contacting a capillary dispenser onto a solid support under conditions effective to draw a defined volume of liquid onto the support, wherein this process is repeated using selected capture antibody dilutions at each selected array position to create a complete array. The method may be practiced in forming a plurality of such arrays, where the solution-depositing step is applied to a selected position on each of a plurality of solid supports at each repeat cycle. A further description of such a method can be found, e.g., in U.S. Pat. No. 5,807,522.

In certain instances, devices for printing on paper can be used to generate the antibody arrays. For example, the desired capture antibody dilution can be loaded into the printhead of a desktop jet printer and printed onto a suitable solid support (see, e.g., Silzel et al., *Clin. Chem.*, 44:2036-2043 (1998)).

In some embodiments, the array generated on the solid support has a density of at least about 5 spots/cm$^2$, and preferably at least about 10, 20, 30, 40, 50, 60, 70, 80, 90, 100, 110, 120, 130, 140, 150, 160, 170, 180, 190, 200, 210, 220, 230, 250, 275, 300, 325, 350, 375, 400, 425, 450, 475, 500, 550, 600, 650, 700, 750, 800, 850, 900, 950, 1000, 2000, 3000, 4000, 5000, 6000, 7000, 8000 or 9000, or 10,000 spots/cm$^2$.

In certain instances, the spots on the solid support each represents a different capture antibody. In certain other instances, multiple spots on the solid support represent the same capture antibody, e.g., as a dilution series comprising a series of descending capture antibody concentrations.

Additional examples of methods for preparing and constructing antibody arrays on solid supports are described in U.S. Pat. Nos. 6,197,599, 6,777,239, 6,780,582, 6,897,073, 7,179,638, and 7,192,720; U.S. Patent Publication Nos. 20060115810, 20060263837, 20060292680, and 20070054326; and Varnum et al., *Methods Mol. Biol.*, 264: 161-172 (2004).

Methods for scanning antibody arrays are known in the art and include, without limitation, any technique used to scan protein or nucleic acid arrays. Microarray scanners suitable for use in the present invention are available from PerkinElmer (Boston, Mass.), Agilent Technologies (Palo Alto, Calif.), Applied Precision (Issaquah, Wash.), GSI Lumonics Inc. (Billerica, Mass.), and Axon Instruments (Union City, Calif.). As a non-limiting example, a GSI ScanArray®3000 for fluorescence detection can be used with ImaGene® software for quantitation.

V. Single Detection Assays

In some embodiments, the assay for detecting the expression and/or activation level of one or more analytes (e.g., one or more signal transduction molecules) of interest in a cellular extract of cells such as tumor cells is a multiplex, high-throughput two-antibody assay having superior dynamic range. As a non-limiting example, the two antibodies used in the assay can comprise: (1) a capture antibody specific for a particular analyte of interest; and (2) a detection antibody specific for an activated form of the analyte (i.e., activation state-dependent antibody). The activation state-dependent antibody is capable of detecting, for example, the phosphorylation, ubiquitination, and/or complexation state of the analyte. Alternatively, the detection antibody comprises an activation state-independent antibody, which detects the total amount of the analyte in the cellular extract. The activation state-independent antibody is generally capable of detecting both the activated and non-activated forms of the analyte.

In one particular embodiment, the two-antibody assay for detecting the expression or activation level of an analyte of interest comprises:
  (i) incubating the cellular extract with one or a plurality of dilution series of capture antibodies to form a plurality of captured analytes;
  (ii) incubating the plurality of captured analytes with detection antibodies specific for the corresponding analytes to form a plurality of detectable captured analytes, wherein the detection antibodies comprise activation state-dependent antibodies for detecting the activation (e.g., phosphorylation) level of the analyte or activation state-independent antibodies for detecting the expression level (e.g., total amount) of the analyte;
(iii) incubating the plurality of detectable captured analytes with first and second members of a signal amplification pair to generate an amplified signal; and
(iv) detecting the amplified signal generated from the first and second members of the signal amplification pair.

The two-antibody assays described herein are typically antibody-based arrays which comprise a plurality of different capture antibodies at a range of capture antibody concentrations that are coupled to the surface of a solid support in different addressable locations. Examples of suitable solid supports for use in the present invention are described above.

The capture antibodies and detection antibodies are preferably selected to minimize competition between them with respect to analyte binding (i.e., both capture and detection antibodies can simultaneously bind their corresponding signal transduction molecules).

In one embodiment, the detection antibodies comprise a first member of a binding pair (e.g., biotin) and the first member of the signal amplification pair comprises a second member of the binding pair (e.g., streptavidin). The binding pair members can be coupled directly or indirectly to the detection antibodies or to the first member of the signal amplification pair using methods well-known in the art. In certain instances, the first member of the signal amplification pair is a peroxidase (e.g., horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, etc.), and the second member of the signal amplification pair is a tyramide reagent (e.g., biotin-tyramide). In these instances, the amplified signal is generated by peroxidase oxidization of the tyramide reagent to produce an activated tyramide in the presence of hydrogen peroxide ($H_2O_2$).

The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

An exemplary protocol for performing the two-antibody assays described herein is provided in Example 3 of PCT Publication No. WO2009/108637, the disclosure of which is herein incorporated by reference in its entirety for all purposes.

In another embodiment of a two-antibody approach, the present invention provides a method for detecting the expression or activation level of a truncated receptor, the method comprising:
(i) incubating the cellular extract with a plurality of beads specific for an extracellular domain (ECD) binding region of a full-length receptor;
(ii) removing the plurality of beads from the cellular extract, thereby removing the full-length receptor to form a cellular extract devoid of the full-length receptor;
(iii) incubating the cellular extract devoid of the full-length receptor with a dilution series of one or a plurality of capture antibodies specific for an intracellular domain (ICD) binding region of the full-length receptor to form a plurality of captured truncated receptors;
(iv) incubating the plurality of captured truncated receptors with detection antibodies specific for an ICD binding region of the full-length receptor to form a plurality of detectable captured truncated receptors, wherein the detection antibodies comprise activation state-dependent antibodies for detecting the activation (e.g., phosphorylation) level of the truncated receptor or activation state-independent antibodies for detecting the expression level (e.g., total amount) of the truncated receptor;
(v) incubating the plurality of detectable captured truncated receptors with first and second members of a signal amplification pair to generate an amplified signal; and
(vi) detecting an amplified signal generated from the first and second members of the signal amplification pair.

In certain embodiments, the truncated receptor is p95HER2 and the full-length receptor is HER2. In certain other embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

FIG. 14A of PCT Publication No. WO2009/108637, the disclosure of which is herein incorporated by reference in its entirety for all purposes, shows that beads coated with an antibody directed to the extracellular domain (ECD) of a receptor of interest binds the full-length receptor (e.g., HER2), but not the truncated receptor (e.g., p95HER2) to remove any full-length receptor from the assay. FIG. 14B of PCT Publication No. WO2009/108637 shows that the truncated receptor (e.g., p95HER2), once bound to a capture antibody, may then be detected by a detection antibody that is specific for the intracellular domain (ICD) of the full-length receptor (e.g., HER2). The detection antibody may be directly conjugated to horseradish peroxidase (HRP). Tyramide signal amplification (TSA) may then be performed to generate a signal to be detected. The expression level or activation state of the truncated receptor (e.g., p95HER2) can be interrogated to determine, e.g., its total concentration or its phosphorylation state, ubiquitination state, and/or complexation state.

In another embodiment, the present invention provides kits for performing the two-antibody assays described above comprising: (a) a dilution series of one or a plurality of capture antibodies restrained on a solid support; and (b) one or a plurality of detection antibodies (e.g., activation state-independent antibodies and/or activation state-dependent antibodies). In some instances, the kits can further contain instructions for methods of using the kit to detect the expression levels and/or activation states of one or a plurality of signal transduction molecules of cells such as tumor cells. The kits may also contain any of the additional reagents described above with respect to performing the specific methods of the present invention such as, for example, first and second members of the signal amplification pair, tyramide signal amplification reagents, wash buffers, etc.

VI. Proximity Dual Detection Assays

In some embodiments, the assay for detecting the expression and/or activation level of one or more analytes (e.g., one or more signal transduction molecules) of interest in a cellular extract of cells such as tumor cells is a multiplex, high-throughput proximity (i.e., three-antibody) assay having superior dynamic range. As a non-limiting example, the three antibodies used in the proximity assay can comprise: (1) a capture antibody specific for a particular analyte of interest; (2) a detection antibody specific for an activated form of the analyte (i.e., activation state-dependent antibody); and (3) a detection antibody which detects the total amount of the analyte (i.e., activation state-independent antibody). The activation state-dependent antibody is capable of detecting, e.g., the phosphorylation, ubiquitination, and/or complexation state of the analyte, while the activation state-independent antibody is capable of detecting the total amount (i.e., both the activated and non-activated forms) of the analyte.

In one particular embodiment, the proximity assay for detecting the activation level or status of an analyte of interest comprises:
  (i) incubating the cellular extract with one or a plurality of dilution series of capture antibodies to form a plurality of captured analytes;
  (ii) incubating the plurality of captured analytes with detection antibodies comprising one or a plurality of activation state-independent antibodies and one or a plurality of activation state-dependent antibodies specific for the corresponding analytes to form a plurality of detectable captured analytes, wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
  (iii) incubating the plurality of detectable captured analytes with a second member of the signal amplification pair to generate an amplified signal; and
  (iv) detecting the amplified signal generated from the first and second members of the signal amplification pair.

In another particular embodiment, the proximity assay for detecting the activation level or status of an analyte of interest that is a truncated receptor comprises:
  (i) incubating the cellular extract with a plurality of beads specific for an extracellular domain (ECD) binding region of a full-length receptor;
  (ii) removing the plurality of beads from the cellular extract, thereby removing the full-length receptor to form a cellular extract devoid of the full-length receptor;
  (iii) incubating the cellular extract devoid of the full-length receptor with one or a plurality of capture antibodies specific for an intracellular domain (ICD) binding region of the full-length receptor to form a plurality of captured truncated receptors;
  (iv) incubating the plurality of captured truncated receptors with detection antibodies comprising one or a plurality of activation state-independent antibodies and one or a plurality of activation state-dependent antibodies specific for an ICD binding region of the full-length receptor to form a plurality of detectable captured truncated receptors,
  wherein the activation state-independent antibodies are labeled with a facilitating moiety, the activation state-dependent antibodies are labeled with a first member of a signal amplification pair, and the facilitating moiety generates an oxidizing agent which channels to and reacts with the first member of the signal amplification pair;
  (v) incubating the plurality of detectable captured truncated receptors with a second member of the signal amplification pair to generate an amplified signal; and
  (vi) detecting the amplified signal generated from the first and second members of the signal amplification pair.

In certain embodiments, the truncated receptor is p95HER2 and the full-length receptor is HER2. In certain other embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

In alternative embodiments, the activation state-dependent antibodies can be labeled with a facilitating moiety and the activation state-independent antibodies can be labeled with a first member of a signal amplification pair.

As another non-limiting example, the three antibodies used in the proximity assay can comprise: (1) a capture antibody specific for a particular analyte of interest; (2) a first detection antibody which detects the total amount of the analyte (i.e., a first activation state-independent antibody); and (3) a second detection antibody which detects the total amount of the analyte (i.e., a second activation state-independent antibody). In preferred embodiments, the first and second activation state-independent antibodies recognize different (e.g., distinct) epitopes on the analyte.

In one particular embodiment, the proximity assay for detecting the expression level of an analyte of interest comprises:
  (i) incubating the cellular extract with one or a plurality of dilution series of capture antibodies to form a plurality of captured analytes;
  (ii) incubating the plurality of captured analytes with detection antibodies comprising one or a plurality of first and second activation state-independent antibodies specific for the corresponding analytes to form a plurality of detectable captured analytes,
  wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;
  (iii) incubating the plurality of detectable captured analytes with a second member of the signal amplification pair to generate an amplified signal; and
  (iv) detecting the amplified signal generated from the first and second members of the signal amplification pair.

In another particular embodiment, the proximity assay for detecting the expression level of an analyte of interest that is a truncated receptor comprises:
  (i) incubating the cellular extract with a plurality of beads specific for an extracellular domain (ECD) binding region of a full-length receptor;

(ii) removing the plurality of beads from the cellular extract, thereby removing the full-length receptor to form a cellular extract devoid of the full-length receptor;

(iii) incubating the cellular extract devoid of the full-length receptor with one or a plurality of capture antibodies specific for an intracellular domain (ICD) binding region of the full-length receptor to form a plurality of captured truncated receptors;

(iv) incubating the plurality of captured truncated receptors with detection antibodies comprising one or a plurality of first and second activation state-independent antibodies specific for an ICD binding region of the full-length receptor to form a plurality of detectable captured truncated receptors, wherein the first activation state-independent antibodies are labeled with a facilitating moiety, the second activation state-independent antibodies are labeled with a first member of a signal amplification pair, and the facilitating moiety generates an oxidizing agent which channels to and reacts with the first member of the signal amplification pair;

(v) incubating the plurality of detectable captured truncated receptors with a second member of the signal amplification pair to generate an amplified signal; and (vi) detecting the amplified signal generated from the first and second members of the signal amplification pair.

In certain embodiments, the truncated receptor is p95HER2 and the full-length receptor is HER2. In certain other embodiments, the plurality of beads specific for an extracellular domain (ECD) binding region comprises a streptavidin-biotin pair, wherein the biotin is attached to the bead and the biotin is attached to an antibody (e.g., wherein the antibody is specific for the ECD binding region of the full-length receptor).

In alternative embodiments, the first activation state-independent antibodies can be labeled with a first member of a signal amplification pair and the second activation state-independent antibodies can be labeled with a facilitating moiety.

The proximity assays described herein are typically antibody-based arrays which comprise one or a plurality of different capture antibodies at a range of capture antibody concentrations that are coupled to the surface of a solid support in different addressable locations. Examples of suitable solid supports for use in the present invention are described above.

The capture antibodies, activation state-independent antibodies, and activation state-dependent antibodies are preferably selected to minimize competition between them with respect to analyte binding (i.e., all antibodies can simultaneously bind their corresponding signal transduction molecules).

In some embodiments, activation state-independent antibodies for detecting activation levels of one or more of the analytes or, alternatively, first activation state-independent antibodies for detecting expression levels of one or more of the analytes further comprise a detectable moiety. In such instances, the amount of the detectable moiety is correlative to the amount of one or more of the analytes in the cellular extract. Examples of detectable moieties include, but are not limited to, fluorescent labels, chemically reactive labels, enzyme labels, radioactive labels, and the like. Preferably, the detectable moiety is a fluorophore such as an Alexa Fluor® dye (e.g., Alexa Fluor®647), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The detectable moiety can be coupled directly or indirectly to the activation state-independent antibodies using methods well-known in the art.

In certain instances, activation state-independent antibodies for detecting activation levels of one or more of the analytes or, alternatively, first activation state-independent antibodies for detecting expression levels of one or more of the analytes are directly labeled with the facilitating moiety. The facilitating moiety can be coupled to activation state-independent antibodies using methods well-known in the art. A suitable facilitating moiety for use in the present invention includes any molecule capable of generating an oxidizing agent which channels to (i.e., is directed to) and reacts with (i.e., binds, is bound by, or forms a complex with) another molecule in proximity (i.e., spatially near or close) to the facilitating moiety. Examples of facilitating moieties include, without limitation, enzymes such as glucose oxidase or any other enzyme that catalyzes an oxidation/reduction reaction involving molecular oxygen ($O_2$) as the electron acceptor, and photosensitizers such as methylene blue, rose bengal, porphyrins, squarate dyes, phthalocyanines, and the like. Non-limiting examples of oxidizing agents include hydrogen peroxide ($H_2O_2$), a singlet oxygen, and any other compound that transfers oxygen atoms or gains electrons in an oxidation/reduction reaction. Preferably, in the presence of a suitable substrate (e.g., glucose, light, etc.), the facilitating moiety (e.g., glucose oxidase, photosensitizer, etc.) generates an oxidizing agent (e.g., hydrogen peroxide ($H_2O_2$), single oxygen, etc.) which channels to and reacts with the first member of the signal amplification pair (e.g., horseradish peroxidase (HRP), hapten protected by a protecting group, an enzyme inactivated by thioether linkage to an enzyme inhibitor, etc.) when the two moieties are in proximity to each other.

In certain other instances, activation state-independent antibodies for detecting activation levels of one or more of the analytes or, alternatively, first activation state-independent antibodies for detecting expression levels of one or more of the analytes are indirectly labeled with the facilitating moiety via hybridization between an oligonucleotide linker conjugated to the activation state-independent antibodies and a complementary oligonucleotide linker conjugated to the facilitating moiety. The oligonucleotide linkers can be coupled to the facilitating moiety or to the activation state-independent antibodies using methods well-known in the art. In some embodiments, the oligonucleotide linker conjugated to the facilitating moiety has 100% complementarity to the oligonucleotide linker conjugated to the activation state-independent antibodies. In other embodiments, the oligonucleotide linker pair comprises at least one, two, three, four, five, six, or more mismatch regions, e.g., upon hybridization under stringent hybridization conditions. One skilled in the art will appreciate that activation state-independent antibodies specific for different analytes can either be conjugated to the same oligonucleotide linker or to different oligonucleotide linkers.

The length of the oligonucleotide linkers that are conjugated to the facilitating moiety or to the activation state-independent antibodies can vary. In general, the linker sequence can be at least about 5, 10, 15, 20, 25, 30, 35, 40, 45, 50, 75, or 100 nucleotides in length. Typically, random nucleic acid sequences are generated for coupling. As a non-limiting example, a library of oligonucleotide linkers can be designed to have three distinct contiguous domains: a spacer domain; signature domain; and conjugation domain. Preferably, the oligonucleotide linkers are designed for efficient coupling without destroying the function of the facilitating moiety or activation state-independent antibodies to which they are conjugated.

The oligonucleotide linker sequences can be designed to prevent or minimize any secondary structure formation under a variety of assay conditions. Melting temperatures are typically carefully monitored for each segment within the linker to allow their participation in the overall assay procedures. Generally, the range of melting temperatures of the segment of the linker sequence is between 1-10° C. Computer algorithms (e.g., OLIGO 6.0) for determining the melting temperature, secondary structure, and hairpin structure under defined ionic concentrations can be used to analyze each of the three different domains within each linker. The overall combined sequences can also be analyzed for their structural characterization and their comparability to other conjugated oligonucleotide linker sequences, e.g., whether they will hybridize under stringent hybridization conditions to a complementary oligonucleotide linker.

The spacer region of the oligonucleotide linker provides adequate separation of the conjugation domain from the oligonucleotide crosslinking site. The conjugation domain functions to link molecules labeled with a complementary oligonucleotide linker sequence to the conjugation domain via nucleic acid hybridization. The nucleic acid-mediated hybridization can be performed either before or after antibody-analyte (i.e., antigen) complex formation, providing a more flexible assay format. Unlike many direct antibody conjugation methods, linking relatively small oligonucleotides to antibodies or other molecules has minimal impact on the specific affinity of antibodies towards their target analyte or on the function of the conjugated molecules.

In some embodiments, the signature sequence domain of the oligonucleotide linker can be used in complex multiplexed protein assays. Multiple antibodies can be conjugated with oligonucleotide linkers with different signature sequences. In multiplex immunoassays, reporter oligonucleotide sequences labeled with appropriate probes can be used to detect cross-reactivity between antibodies and their antigens in the multiplex assay format.

Oligonucleotide linkers can be conjugated to antibodies or other molecules using several different methods. For example, oligonucleotide linkers can be synthesized with a thiol group on either the 5' or 3' end. The thiol group can be deprotected using reducing agents (e.g., TCEP-HCl) and the resulting linkers can be purified by using a desalting spin column. The resulting deprotected oligonucleotide linkers can be conjugated to the primary amines of antibodies or other types of proteins using heterobifunctional cross linkers such as SMCC. Alternatively, 5'-phosphate groups on oligonucleotides can be treated with water-soluble carbodiimide EDC to form phosphate esters and subsequently coupled to amine-containing molecules. In certain instances, the diol on the 3'-ribose residue can be oxidized to aldehyde groups and then conjugated to the amine groups of antibodies or other types of proteins using reductive amination. In certain other instances, the oligonucleotide linker can be synthesized with a biotin modification on either the 3' or 5' end and conjugated to streptavidin-labeled molecules.

Oligonucleotide linkers can be synthesized using any of a variety of techniques known in the art, such as those described in Usman et al., *J. Am. Chem. Soc.*, 109:7845 (1987); Scaringe et al., *Nucl. Acids Res.*, 18:5433 (1990); Wincott et al., *Nucl. Acids Res.*, 23:2677-2684 (1995); and Wincott et al., *Methods Mol. Bio.*, 74:59 (1997). In general, the synthesis of oligonucleotides makes use of common nucleic acid protecting and coupling groups, such as dimethoxytrityl at the 5'-end and phosphoramidites at the 3'-end. Suitable reagents for oligonucleotide synthesis, methods for nucleic acid deprotection, and methods for nucleic acid purification are known to those of skill in the art.

In certain instances, activation state-dependent antibodies for detecting activation levels of one or more of the analytes or, alternatively, second activation state-independent antibodies for detecting expression levels of one or more of the analytes are directly labeled with the first member of the signal amplification pair. The signal amplification pair member can be coupled to activation state-dependent antibodies to detect activation levels or second activation state-independent antibodies to detect expression levels using methods well-known in the art. In certain other instances, activation state-dependent antibodies or second activation state-independent antibodies are indirectly labeled with the first member of the signal amplification pair via binding between a first member of a binding pair conjugated to the activation state-dependent antibodies or second activation state-independent antibodies and a second member of the binding pair conjugated to the first member of the signal amplification pair. The binding pair members (e.g., biotin/streptavidin) can be coupled to the signal amplification pair member or to the activation state-dependent antibodies or second activation state-independent antibodies using methods well-known in the art. Examples of signal amplification pair members include, but are not limited to, peroxidases such horseradish peroxidase (HRP), catalase, chloroperoxidase, cytochrome c peroxidase, eosinophil peroxidase, glutathione peroxidase, lactoperoxidase, myeloperoxidase, thyroid peroxidase, deiodinase, and the like. Other examples of signal amplification pair members include haptens protected by a protecting group and enzymes inactivated by thioether linkage to an enzyme inhibitor.

In one example of proximity channeling, the facilitating moiety is glucose oxidase (GO) and the first member of the signal amplification pair is horseradish peroxidase (HRP). When the GO is contacted with a substrate such as glucose, it generates an oxidizing agent (i.e., hydrogen peroxide ($H_2O_2$)). If the HRP is within channeling proximity to the GO, the $H_2O_2$ generated by the GO is channeled to and complexes with the HRP to form an HRP-$H_2O_2$ complex, which, in the presence of the second member of the signal amplification pair (e.g., a chemiluminescent substrate such as luminol or isoluminol or a fluorogenic substrate such as tyramide (e.g., biotin-tyramide), homovanillic acid, or 4-hydroxyphenyl acetic acid), generates an amplified signal. Methods of using GO and HRP in a proximity assay are described in, e.g., Langry et al., U.S. Dept. of Energy Report No. UCRL-ID-136797 (1999). When biotin-tyramide is used as the second member of the signal amplification pair, the HRP-$H_2O_2$ complex oxidizes the tyramide to generate a reactive tyramide radical that covalently binds nearby nucleophilic residues. The activated tyramide is either directly detected or detected upon the addition of a signal-detecting reagent such as, for example, a streptavidin-labeled fluorophore or a combination of a streptavidin-labeled peroxidase and a chromogenic reagent. Examples of fluorophores suitable for use in the present invention include, but are not limited to, an Alexa Fluor® dye (e.g., Alexa Fluor® 555), fluorescein, fluorescein isothiocyanate (FITC), Oregon Green™; rhodamine, Texas red, tetrarhodamine isothiocynate (TRITC), a CyDye™ fluor (e.g., Cy2, Cy3, Cy5), and the like. The streptavidin label can be coupled directly or indirectly to the fluorophore or peroxidase using methods well-known in the art. Non-limiting examples of chromogenic reagents suitable for use in the present invention include 3,3',5,5'-tetramethylbenzidine (TMB), 3,3'-diaminobenzidine (DAB), 2,2'-azino-bis(3-ethylbenzothiazoline-6-sulfonic acid) (ABTS), 4-chloro-1-napthol (4CN), and/or porphyrinogen.

In another example of proximity channeling, the facilitating moiety is a photosensitizer and the first member of the signal amplification pair is a large molecule labeled with multiple haptens that are protected with protecting groups that prevent binding of the haptens to a specific binding partner (e.g., ligand, antibody, etc.). For example, the signal amplification pair member can be a dextran molecule labeled with protected biotin, coumarin, and/or fluorescein molecules. Suitable protecting groups include, but are not limited to, phenoxy-, analino-, olefin-, thioether-, and selenoether-protecting groups. Additional photosensitizers and protected hapten molecules suitable for use in the proximity assays of the present invention are described in U.S. Pat. No. 5,807,675. When the photosensitizer is excited with light, it generates an oxidizing agent (i.e., singlet oxygen). If the hapten molecules are within channeling proximity to the photosensitizer, the singlet oxygen generated by the photosensitizer is channeled to and reacts with thioethers on the protecting groups of the haptens to yield carbonyl groups (ketones or aldehydes) and sulphinic acid, releasing the protecting groups from the haptens. The unprotected haptens are then available to specifically bind to the second member of the signal amplification pair (e.g., a specific binding partner that can generate a detectable signal). For example, when the hapten is biotin, the specific binding partner can be an enzyme-labeled streptavidin. Exemplary enzymes include alkaline phosphatase, (3-galactosidase, HRP, etc. After washing to remove unbound reagents, the detectable signal can be generated by adding a detectable (e.g., fluorescent, chemiluminescent, chromogenic, etc.) substrate of the enzyme and detected using suitable methods and instrumentation known in the art. Alternatively, the detectable signal can be amplified using tyramide signal amplification and the activated tyramide either directly detected or detected upon the addition of a signal-detecting reagent as described above.

In yet another example of proximity channeling, the facilitating moiety is a photosensitizer and the first member of the signal amplification pair is an enzyme-inhibitor complex. The enzyme and inhibitor (e.g., phosphonic acid-labeled dextran) are linked together by a cleavable linker (e.g., thioether). When the photosensitizer is excited with light, it generates an oxidizing agent (i.e., singlet oxygen). If the enzyme-inhibitor complex is within channeling proximity to the photosensitizer, the singlet oxygen generated by the photosensitizer is channeled to and reacts with the cleavable linker, releasing the inhibitor from the enzyme, thereby activating the enzyme. An enzyme substrate is added to generate a detectable signal, or alternatively, an amplification reagent is added to generate an amplified signal.

In a further example of proximity channeling, the facilitating moiety is HRP, the first member of the signal amplification pair is a protected hapten or an enzyme-inhibitor complex as described above, and the protecting groups comprise p-alkoxy phenol. The addition of phenylenediamine and $H_2O_2$ generates a reactive phenylene diimine which channels to the protected hapten or the enzyme-inhibitor complex and reacts with p-alkoxy phenol protecting groups to yield exposed haptens or a reactive enzyme. The amplified signal is generated and detected as described above (see, e.g., U.S. Pat. Nos. 5,532,138 and 5,445,944).

An exemplary protocol for performing the proximity assays described herein is provided in Example 4 of PCT Publication No. WO2009/108637, the disclosure of which is herein incorporated by reference in its entirety for all purposes.

In another embodiment, the present invention provides kits for performing the proximity assays described above comprising: (a) a dilution series of one or a plurality of capture antibodies restrained on a solid support; and (b) one or a plurality of detection antibodies (e.g., a combination of activation state-independent antibodies and activation state-dependent antibodies for detecting activation levels and/or a combination of first and second activation state-independent antibodies for detecting expression levels). In some instances, the kits can further contain instructions for methods of using the kit to detect the expression and/or activation status of one or a plurality of signal transduction molecules of cells such as tumor cells. The kits may also contain any of the additional reagents described above with respect to performing the specific methods of the present invention such as, for example, first and second members of the signal amplification pair, tyramide signal amplification reagents, substrates for the facilitating moiety, wash buffers, etc.

VII. Production of Antibodies

The generation and selection of antibodies not already commercially available for analyzing the levels of expression and activation of signal transduction molecules in tumor cells in accordance with the immunoassays of the present invention can be accomplished several ways. For example, one way is to express and/or purify a polypeptide of interest (i.e., antigen) using protein expression and purification methods known in the art, while another way is to synthesize the polypeptide of interest using solid phase peptide synthesis methods known in the art. See, e.g., *Guide to Protein Purification*, Murray P. Deutcher, ed., *Meth. Enzymol.*, Vol. 182 (1990); Solid Phase Peptide Synthesis, Greg B. Fields, ed., *Meth. Enzymol.*, Vol. 289 (1997); Kiso et al., *Chem. Pharm. Bull.*, 38:1192-99 (1990); Mostafavi et al., *Biomed. Pept. Proteins Nucleic Acids*, 1:255-60, (1995); and Fujiwara et al., *Chem. Pharm. Bull.*, 44:1326-31 (1996). The purified or synthesized polypeptide can then be injected, for example, into mice or rabbits, to generate polyclonal or monoclonal antibodies. One skilled in the art will recognize that many procedures are available for the production of antibodies, for example, as described in *Antibodies, A Laboratory Manual*, Harlow and Lane, Eds., Cold Spring Harbor Laboratory, Cold Spring Harbor, N.Y. (1988). One skilled in the art will also appreciate that binding fragments or Fab fragments which mimic (e.g., retain the functional binding regions of) antibodies can also be prepared from genetic information by various procedures. See, e.g., Antibody Engineering: *A Practical Approach*, Borrebaeck, Ed., Oxford University Press, Oxford (1995); and Huse et al., *J. Immunol.*, 149:3914-3920 (1992).

Those skilled in the art will recognize that many approaches can be taken in producing antibodies or binding fragments and screening and selecting for affinity and specificity for the various polypeptides of interest, but these approaches do not change the scope of the present invention.

A more detailed description of polyclonal antibodies, monoclonal antibodies, humanized antibodies, human antibodies, bispecific antibodies, fragments thereof, and methods of purifying antibodies is found in PCT Publication No.

WO 2010/132723, the disclosure of which is herein incorporated by reference in its entirety for all purposes.

VIII. Methods of Administration

According to the methods of the present invention, the anticancer drugs described herein are administered to a subject by any convenient means known in the art. The methods of the present invention can be used to select a suitable anticancer drug or combination of anticancer drugs for the treatment of a tumor, e.g., a breast tumor such as a triple-negative metastatic breast tumor, in a subject. The methods of the present invention can also be used to predict the response of a tumor, e.g., a breast tumor such as a triple-negative metastatic breast tumor, to treatment with an anticancer drug or combination of anticancer drugs. In addition, the methods of the present invention can be used to determine the sensitivity of a tumor cell such as a triple-negative tumor cell, e.g., from a triple-negative metastatic breast tumor, to treatment with an anticancer drug or combination of anticancer drugs. One skilled in the art will appreciate that the anticancer drugs described herein can be administered alone or as part of a combined therapeutic approach with conventional chemotherapy, radiotherapy, hormonal therapy, immunotherapy, and/or surgery.

In certain embodiments, the anticancer drug comprises an anti-signaling agent (i.e., a cytostatic drug) such as a monoclonal antibody or a tyrosine kinase inhibitor; an anti-proliferative agent; a chemotherapeutic agent (i.e., a cytotoxic drug); a hormonal therapeutic agent; a radiotherapeutic agent; a vaccine; and/or any other compound with the ability to reduce or abrogate the uncontrolled growth of aberrant cells such as cancerous cells. In some embodiments, the subject is treated with one or more anti-signaling agents, anti-proliferative agents, and/or hormonal therapeutic agents in combination with at least one chemotherapeutic agent. Exemplary monoclonal antibodies, tyrosine kinase inhibitors, anti-proliferative agents, chemotherapeutic agents, hormonal therapeutic agents, radiotherapeutic agents, and vaccines are described above.

In preferred embodiments, the anticancer drug is a combination of bevacizumab (Avastin®), carboplatin, and paclitaxel ("triplet therapy"). In some instances, the paclitaxel is a nanoparticle albumin-bound (nab) paclitaxel (Abraxane® or nabP). In other embodiments, the anticancer drug comprises iniparib (BSI 201; 4-iodo-3-nitrobenzamide), NKO12 (an SN-38-releasing nanodevice constructed by covalently attaching SN-38 to the block copolymer PEG-PGlu, followed by self-assembly of amphiphilic block copolymers in aqueous media), glembatumumab vedotin, (also known as CDX-011 or CR011-vcMMAE; human monoclonal antibody glembatumumab (CR011) linked to monomethyl auristatin E (MMAE) that targets cancer cells expressing transmembrane glycoprotein NMB), or combinations thereof. In one particular embodiment, the anticancer drug is a combination of iniparib (a PARP inhibitor), gemcitabine (Gemzar®), and carboplatin.

In some embodiments, the anticancer drugs described herein can be co-administered with conventional immunotherapeutic agents including, but not limited to, immunostimulants (e.g., *Bacillus* Calmette-Guerin (BCG), levamisole, interleukin-2, alpha-interferon, etc.), immunotoxins (e.g., anti-CD33 monoclonal antibody-calicheamicin conjugate, anti-CD22 monoclonal antibody-*pseudomonas* exotoxin conjugate, etc.), and radioimmunotherapy (e.g., anti-CD20 monoclonal antibody conjugated to $^{111}$In, $^{90}$Y, or $^{131}$I, etc.).

Anticancer drugs can be administered with a suitable pharmaceutical excipient as necessary and can be carried out via any of the accepted modes of administration. Thus, administration can be, for example, oral, buccal, sublingual, gingival, palatal, intravenous, topical, subcutaneous, transcutaneous, transdermal, intramuscular, intra-joint, parenteral, intra-arteriole, intradermal, intraventricular, intracranial, intraperitoneal, intravesical, intrathecal, intralesional, intranasal, rectal, vaginal, or by inhalation. By "co-administer" it is meant that an anticancer drug is administered at the same time, just prior to, or just after the administration of a second drug (e.g., another anticancer drug, a drug useful for reducing the side-effects associated with anticancer drug therapy, a radiotherapeutic agent, a hormonal therapeutic agent, an immunotherapeutic agent, etc.).

A therapeutically effective amount of an anticancer drug may be administered repeatedly, e.g., at least 2, 3, 4, 5, 6, 7, 8, or more times, or the dose may be administered by continuous infusion. The dose may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for human subjects and other mammals, each unit containing a predetermined quantity of an anticancer drug calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus will contain substantially more than, e.g., at least 1, 2, 3, 4, 5, 6, 7, 8, 9, 10, or more times the amount of the anticancer drug.

Methods for preparing such dosage forms are known to those skilled in the art (see, e.g., REMINGTON'S PHARMACEUTICAL SCIENCES, 18TH ED., Mack Publishing Co., Easton, Pa. (1990)). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., REMINGTON'S PHARMACEUTICAL SCIENCES, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the therapeutically effective dose takes the form of a pill, tablet, or capsule, and thus, the dosage form can contain, along with an anticancer drug, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. An anticancer drug can also be formulated into a suppository disposed, for example, in a polyethylene glycol (PEG) carrier.

Liquid dosage forms can be prepared by dissolving or dispersing an anticancer drug and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. An anticancer drug can also be formulated into a retention enema.

For topical administration, the therapeutically effective dose can be in the form of emulsions, lotions, gels, foams, creams, jellies, solutions, suspensions, ointments, and transdermal patches. For administration by inhalation, an anticancer drug can be delivered as a dry powder or in liquid form via a nebulizer. For parenteral administration, the therapeutically effective dose can be in the form of sterile injectable solutions and sterile packaged powders. Preferably, injectable solutions are formulated at a pH of from about 4.5 to about 7.5.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to a subject.

A subject can also be monitored at periodic time intervals to assess the efficacy of a certain therapeutic regimen. For example, the expression and/or activation levels of certain signal transduction molecules may change based on the therapeutic effect of treatment with one or more of the anticancer drugs described herein. The subject can be monitored to assess response and understand the effects of certain drugs or treatments in an individualized approach. Additionally, subjects who initially respond to a specific anticancer drug or combination of anticancer drugs may become refractory to the drug or drug combination, indicating that these subjects have developed acquired drug resistance. These subjects can be discontinued on their current therapy and an alternative treatment prescribed in accordance with the methods of the present invention.

In certain aspects, the methods described herein can be used in conjunction with panels of gene expression markers that predict the likelihood of breast cancer prognosis and/or recurrence in various populations. These gene panels can be useful for identifying individuals who are unlikely to experience recurrence and, thus, unlikely to benefit from adjuvant chemotherapy. The expression panels can be used to identify individuals who can safely avoid adjuvant chemotherapy, without negatively affecting disease-free and overall survival outcomes. Suitable systems include, but are not limited to, Oncotype DX™, which is a 21-gene panel from Genomic Health, Inc.; MammaPrint,® which is a 70-gene panel from Agendia; and a 76-gene panel from Veridex.

In addition, in certain other aspects, the methods described herein can be used in conjunction with panels of gene expression markers that identify the original tumors for cancers of unknown primary (CUP). These gene panels can be useful in identifying patients with metastatic cancer who would benefit from therapy consistent with that given to patients diagnosed initially with breast cancer. Suitable systems include, but are not limited to, the Aviara CancerTYPE ID assay, an RT-PCR-based expression assay that measures 92 genes to identify the primary site of origin for 39 tumor types; and the Pathwork® Tissue of Origin Test, which measures the expression of more than 1600 genes on a microarray and compares a tumor's gene expression "signature" against those of 15 known tissue types."

IX. Examples

The following examples are offered to illustrate, but not to limit, the claimed invention.

The Examples from PCT Publication No. WO 2010/132723 are herein incorporated by reference in their entirety for all purposes.

Example 1. Exemplary Proximity Assay Slide Format

This example illustrates one preferred embodiment of the proximity assays of the invention, also known as the Collaborative Enzyme Enhanced Reactive ImmunoAssay (CEER). The proximity assays of this embodiment use an antibody-microarray based platform that measures the expression and activation of target proteins in circulating tumor cells (CTCs) and/or tissue samples (e.g., FNAs). As a non-limiting example, the proximity assays of this embodiment can be used to analyze the level of protein expression and/or the status of activation of one or more target proteins such as HER1 in CTCs or tumor tissue. In some instances, the proximity assays of this embodiment utilize CTCs isolated from about 7.5 ml of whole blood by magnetic particles coated with anti-Ep-CAM antibodies using the CTC-Profiler (Veridex). Isolated CTCs may then be stimulated with growth factors (e.g., EGF+Heregulin) prior to immuno-analysis of subsequent ErbB pathway expression and/or activation. In other instances, the proximity assays of this embodiment utilize tumor tissue samples including fresh frozen metastatic biopsies such as, e.g., triple-negative breast cancer samples.

In certain instances, the proximity assays of this embodiment use a slide format and include multiple calibrators and controls. FIG. 1 shows the array designs of exemplary slide formats for analyzing total and phosphorylated HER1 and HER2 levels. There are 16 pads on each slide with room for 300 spots on each pad. A contact microarray printer was used to print on the 16 pad nitrocellulose slides. Each spot includes a tracking dye and either a specific capture antibody (Ab) or controls printed in triplicates in serial dilutions. The capture Abs are printed at 1 mg/ml, 0.5 mg/ml, and 0.25 mg/ml. Purified IgG was printed as an orientation reference in both the Total and Phospho assays. BSA-phospho was printed as a reagent control. Analytical calibration reactions are performed on 8 pads and internal quality control reactions on 2 pads. Each slide allows processing of up to 4 unknown patient samples. Expression of total target proteins or phosphorylated activated proteins can be reported in Computed Unit (CU), a unit based on calculation from standard curves of diluted lysate from positive cell lines which express the protein of interest. Two separate slides are used for each sample; one slide to detect the expression of the target proteins in cells isolated from whole blood ("Total Assay Slide") and the other for the detection of phosphorylation to detect the degree of target protein activation ("Phospho Assay Slide").

In one embodiment, whole blood from patients and normal control individuals are collected in EDTA tubes. In order to prevent any skin cell contamination during blood draw, our procedures stipulate that the first 3 mL of blood collected is discarded (or collected in CellSave tube for CTC counts and visual immuno-staining using CellSearch kit). Two additional EDTA tubes are then used to collect 7.5 mL of whole blood in each tube. CTCs are then isolated from each tube using an automated magnetic cell separation device (Veridex AutoPrep). Enriched samples are combined and then stimulated with growth factors. Activated cells are then lysed and either immediately processed or stored at −80° C. for subsequent immuno-analysis. In another embodiment, cells from tumor tissue such as fresh frozen metastatic biopsies are obtained, lysed to produce a cellular extract, and then either immediately processed or stored at −80° C. for subsequent immuno-analysis.

Figure 2:
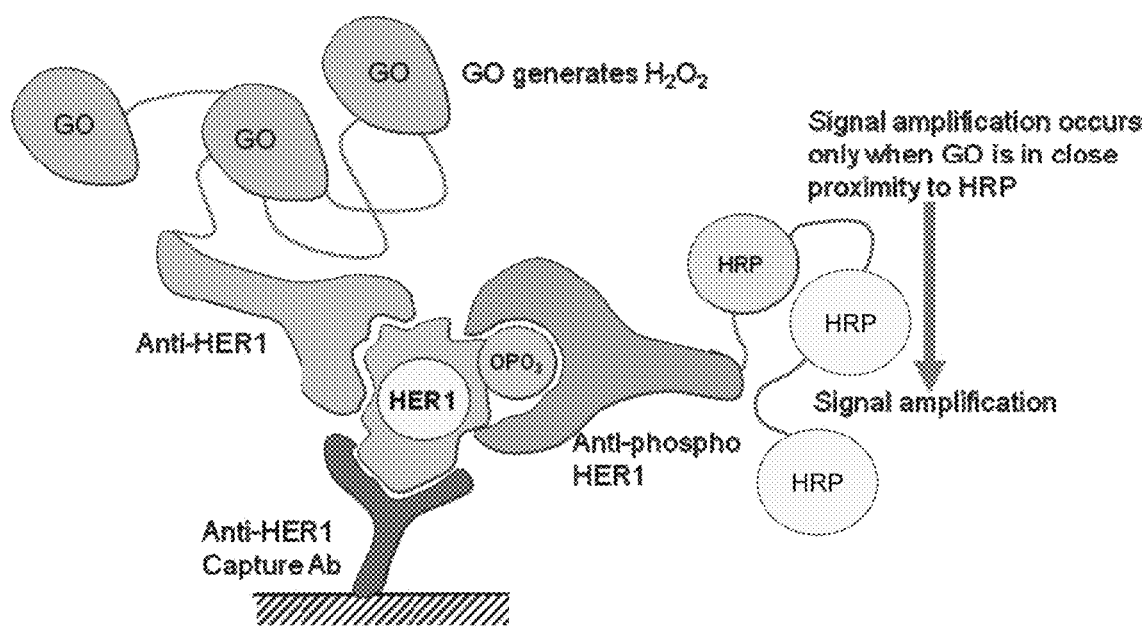
FIG. 2 shows a schematic of an exemplary proximity assay for detecting phosphorylated HER1. GO, glucose oxidase; HRP, horseradish peroxidase.

The proximity assays of this embodiment are initiated by incubating protein targets in cell lysates with capture antibodies on an immuno-microarray surface. Any HER1 or other RTK or signal transduction pathway protein in cell lysates are bound to their corresponding capture antibodies and subsequently unique immuno-complexes are formed by two additional detector antibodies. One of the detector antibodies is conjugated to glucose oxidase (GO) and generates $H_2O_2$ in the presence of glucose. When the second HRP-conjugated detector antibody is bound in proximity within the immuno-complex, a positive signal is generated. The subsequent tyramide-mediated signal amplification process enhances the sensitivity of the assay. The specificity of protein detection is enhanced by the concurrent binding of three specific Abs to different epitopes, and sensitivity can be as high as a single cell due to the amplification. FIG. 2 shows a schematic of an exemplary proximity assay for detecting phosphorylated HER1.

The microarray platform described herein offers the benefit of multiplexing. The ability to expand the assay enables high content analysis with the measurement of multiple receptors and signaling molecules from limited available sample. The microarray is scalable and has the potential for achieving the throughput needed for a clinically useful diagnostic assay.

Example 2. EGFR and VEGFR2 Expression Predict Response to Nab-Paclitaxel (nabP)/Carboplatin (C)/Bevacizumab (B) Chemotherapy in Triple-Negative Metastatic Breast Cancer (TNMBC)

Background

Patients with triple-negative metastatic breast cancer (TNMBC), in which their cancer demonstrates no expression of estrogen, progesterone, or human epidermal growth factor receptor 2 (HER2) receptors, face a poor prognosis (Dent, R. et al., *Clin Cancer Res.* 13(15 Pt 1):4429-4434 (2007)). Improved therapies and predictive markers are needed in this setting.

B (bevacizumab; Avastin®) and C (Carboplatin) combinations are active in many solid tumors, including TNMBC. Nab-paclitaxel (nabP; Abraxane®) potentially targets SPARC, an albumin-binding protein secreted by tumors.

Taxane- and platinum-based chemotherapies have significant activity in the first-line treatment of metastatic breast cancer and are particularly effective when given in combination (Perez, E. A., *Oncologist* 9(5):518-527 (2004); Perez, E. A. et al., *Oncology* 69(2):117-121 (2005); O'Shaughnessy J., *Oncologist* 10(Suppl 3):20-29 (2005)).

Nanoparticle albumin-bound (nab)-paclitaxel has improved efficacy and tolerability compared with standard paclitaxel (Gradishar, W. J. et al., *J Clin Oncol.* 23(31): 7794-7803 (2005)).

Among the platinum agents, carboplatin appears to have similar efficacy and is better tolerated than cisplatin when combined with a taxane, with a lower risk of non-hematologic toxicity, although with a somewhat greater risk of hematologic toxicity (Gainford, C. et al., *Proc Am Soc Clin Oncol.* 19:113, Abstract 439 (2000); Perez, E. A. et al., *Cancer* 88(1):124-131 (2000); Perez, E. A. et al., *Oncology* 69(2):117-121 (2005)). The incidence of neutropenia lessens when carboplatin is combined with paclitaxel rather than docetaxel (Perez, E. A. et al., *Cancer* 88(1):124-131 (2000); Perez, E. A. et al., *Oncology* 69(2):117-121 (2005)).

Bevacizumab is a monoclonal antibody that targets vascular endothelial growth factor (VEGF) to inhibit angiogenesis. Adding bevacizumab to taxane-based chemotherapy significantly improves treatment response rates and progression-free survival (PFS) in women with metastatic breast cancer (Miller, K. D. et al., *N Engl J Med.* 357(26):2666-2676 (2007); Miles, D. W. et al., *Cancer Res.* 69(24S):495s, Abstract 41 (2009); Robert, N. J. et al., *J Clin Oncol.* 27(15 suppl):42s, Abstract 1005 (2009)).

Objective

This study used enrollment metastatic biopsies (bxs) of untreated TNMBC to (1) describe expression/activation of signaling pathways in TNMBC, and (2) correlate these expression patterns in TNMBC with response.

Methods

Fresh frozen metastatic biopsies obtained at trial initiation were used to assess the expression and activation of signaling pathway proteins (e.g., HER1 (EGFR), HER2, HER3, insulin-like growth factor receptor 1 (IGF1-R), c-KIT, c-MET, PI3K, AKT, MAPK, and/or VEGFR2). A proximity assay platform such as CEER was used to determine comprehensive pathway protein expression and activation. The log-rank test was used to test the association between progression free survival (PFS) and protein expression or activation of the pathway proteins. The tumor tissue samples used in this study were obtained from an ongoing clinical trial entitled "A Phase II Study of Abraxane®, Carboplatin and Bevacizumab [triplet therapy] in 'Triple Negative' (Demonstrating No Expression for Estrogen, Progesterone, or Her2 Receptors) Metastatic Breast Cancer" with the following ClinicalTrials.gov identifier: NCT00479674, the disclosure of which is herein incorporated by reference in its entirety for all purposes.

Results

Total EGFR was expressed in 11/18 (61%) biopsies, but was activated in 3/18 (17%). PI3K and AKT were overexpressed in 11/18 (61%) and 8/18 (44%) patients, respectively, and were co-expressed in 6/18 (33%) biopsies. In 17 metastatic biopsies, there was higher total EGFR expression (33 wks vs. 22 wks, p=0.14) and lower expression of VEGFR2 (33 wks vs. 18 wks, p=0.16). All measurements were performed by CEER.

Conclusions

Nab-Paclitaxel/Carboplatin/Bevacuzimab offers a well tolerated and effective therapy for TNMBC. Overexpression of total EGFR and lower VEGFR2 levels offer predictive value for response to triplet therapy in TNMBC. Real-time metastatic biopsies indicate that important changes occur between primary and metastatic tumors, and these changes are highly influential in defining predictive markers of response for TNMBC.

Example 3. Comprehensive Pathway Profiling to Predict Response to Therapy Containing Carboplatin (C)/Bevacizumab (B) in Triple-Negative Metastatic Breast Cancer (TNMBC)

Background: Improved therapies and predictive markers are needed in TNMBC. B (Avastin®) and C (Carboplatin) combinations are active in many solid tumors, including TNBC. This study used archival primary and metastatic biopsies (bxs) of untreated TNMBC (1) to determine the level of expression of VEGFR2 in primary and TNMBC, (2) to describe expression/activation of various signaling pathway proteins in TNMBC, and (3) to correlate these expression patterns in TNMBC with response.

Methods: Triple negative breast cancer core-biopsy specimens were collected and appropriately frozen at −80° C. A novel immunoassay method was applied to investigate the levels of expression and activation of signaling proteins in 1000 ng to 5000 ng of frozen tissues. The CEER platform (aka COPIA) is a multiplexed immuno-microarray platform that utilizes the formation of a unique immuno-complex requiring the co-localization of two detector-antibodies for channeling events for signal generation/amplification resulting in extremely high analytical sensitivity and specificity.

Results: This study identified varying degrees of CK values in each specimen (from approximately 3 to 1000 tumor cells/1000 ng to 5000 ng of cell lysate). In these TNMBCs, HER2 expression levels ranged from low to moderate (0 to 2+, IHC equivalent) and were found in 17 out of 18 samples. One out of 18 samples had substantially high levels of HER2 expression (IHC 3+ level). 50% of the specimens did not show HER2 phosphorylation while the other 50% showed varying levels of activated HER2. The prevalence of HER1, HER3, IGF1-R, c-KIT, c-MET, PI3K, Shc, VEGFR2, and AKT expression/activation was also analyzed in these samples.

Conclusion: Real-time metastatic biopsies indicate that important changes occur between primary and metastatic tumors, and these changes are highly influential in defining predictive markers of response. Over-expression of total and activated EGFR, and lower VEGFR2 levels offer predictive value for response to triplet therapy (B+C+ Nab-paclitaxel) in TNMBC. As disease-profile often shifts, monitoring of alterations in transduction pathway proteins will be useful for therapy adjustments.

Example 4. Functional Profiling of Multiple Signal Pathway Proteins in Breast Cancer Patients Abstract One of the mechanisms of de novo or acquired resistance is the expression of various forms of truncated HER2/ERBB2 receptors ("t-ERBB2") with missing amino-terminal extracellular domains. Non-limiting examples of t-ERBB2 isoforms include p110, p95HER2 (p95m), p95c, and p95n. Methods for profiling various forms of HER2 receptors and other receptor tyrosine kinases (RTKs) with transactivation potential in primary and metastatic tumors may provide valuable insight into the shifting disease pathogenesis. This example describes the successful profiling of a panel of signal transduction pathway proteins for their expression and activation in 230 breast cancer with various ER/PR/HER2 status. In particular, the levels of total and phosphorylated t-ERBB2 species in human breast tumor samples were investigated using the novel proximity mediated immuno-microarray method described herein. This example shows that t-ERBB2 isoforms were detected in strongly ERBB2 positive tumors (16 of 31 samples, 52%) and were phosphorylated in 10 of 38 samples (32%).

Introduction

Several mechanisms for Trastuzumab resistance have been reported. Primarily, the activation of other RTKs (such as IGF1-R) and the accumulation of truncated forms of HER2 have been frequently reported, among other mechanisms. In particular, the amino terminally truncated carboxyl terminal fragments of HER2, collectively known as p95HER2, are frequently found in HER2-expressing breast cancer cell lines and tumors. Cross-talk between various signal transduction pathways and feedback loops provide escape mechanisms for tumors under certain therapeutic pressure or pathway addiction and requires a comprehensive diagnostic tool to perform "pathway network analysis." Treatment decisions made based on clinical information obtained through current IHC/FISH-based technology performed for a few selected biomarkers will not be effective in treating patients with rapidly evolving heterogeneous disease. This example demonstrates that a different configuration of detector antibodies allows differential detection of truncated targets (e.g., p95HER2) from their full-length counterparts (e.g., HER2). In particular, this example illustrates the use of a novel, highly sensitive and specific antibody microarray format, Collaborative Enzyme Enhanced Reactive ImmunoAssay (CEER), to quantify the levels of total and phosphorylated t-ERBB2 species in human samples, in both flash frozen tissue and fine-needle aspirates of metastatic tumors. This example further demonstrates an analysis of the functional status (expression and activation) of HER2, p95HER2, HER1, HER3, and IGF1R as well as the downstream signal transduction proteins PI3K, Shc, and c-MET.

Methods

Multiplexed microarray printing: Capture antibodies (Abs) were printed on nitrocellulose-coated glass slides (ONCYTE®, Grace Bio-Labs) using non-contact printers (Nanoplotter, GeSiM). The spot diameter was approximately 175 µm and printed slides were kept in a desiccated chamber at 4° C. Each spot included a tracking dye and specific capture Abs. Approximately 500 pL of capture Abs were printed in triplicate and at serial dilution concentrations of 1 mg/mL, 0.5 mg/mL, and 0.25 mg/mL. Purified mouse-IgGs were printed as a negative control. Each slide contains cell line controls for standard curve generation for accurate quantitation of samples on each slide run. Internal quality control samples are run on each slide to ensure the quality of data generated from each array-slide.

Antibody conjugation and purification: Target-specific Abs and corresponding detector enzymes were activated with a bi-functional cross-linker, succinimidyl-4-(N-maleimidomethyl) cyclohexane-1-carboxylate (SMCC), and coupled to dextran to make antibody-dextran-enzyme polymer conjugates. The conjugate was purified by HPLC using a size-exclusion column. The Ab activities in the purified conjugates were detected by competition ELISA and enzyme activity was detected by a functional assay specific for each detector enzyme.

Figure 3:
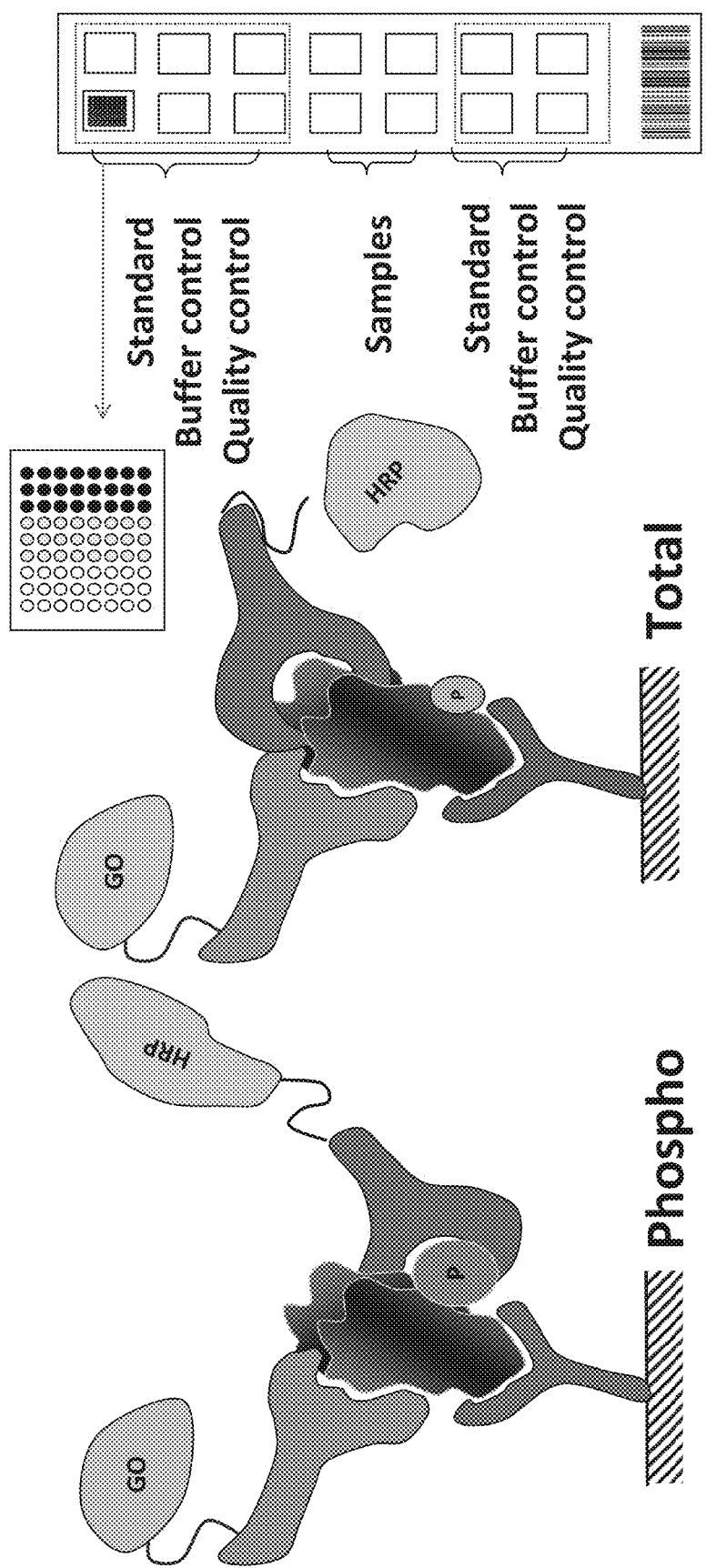
FIG. 3 shows a schematic of the Collaborative Enzyme Enhanced Reactive ImmunoAssay (CEER), also known as the COllaborative Proximity ImmunoAssay (COPIA). When target proteins are bound to specific capture antibodies printed on nitrocellulose surface after incubating with cell lysate, unbound non-target proteins are removed from the slide. One of the detector antibodies against alternate epitope on captured target-protein are conjugated with GO. Binding of another detector antibodies specific to phosphorylated sites on target protein (P) or another non-overlapping epitope (p) conjugated with HRP completes the formation of immuno-complex necessary for signal generation and subsequent tyramide mediated signal amplification through GO-HRP enzyme channeling in the presence of glucose. The capture and detection antibodies were selected to minimize competition between them (i.e., all antibodies can simultaneously bind their corresponding epitope on the signal transduction protein).

Collaborative Enzyme Enhanced Reactive ImmunoAssay (CEER): As depicted in FIG. 3, target proteins present in tissue lysates are bound to specific capture antibodies printed on the nitrocellulose surface and unbound non-target proteins are removed from the slide. The enzymatic interaction between one detector antibody against an alternate epitope on a captured target protein conjugated to Glucose Oxidase (GO) and the other detector antibody specific for a phosphorylated site on the target protein or another non-overlapping epitope conjugated to HRP results in signal generation and subsequent tyramide-mediated signal amplification. In particular, the immuno-microarray slides were rinsed 2 times with TBST (50 mM Tris/150 mM NaCl/0.1% Tween-20, pH 7.2-7.4), blocked with 80 μL of Whatman Blocking Buffer for 1 hr at RT, and then washed 2 times with TBST. Serially diluted cell lysate controls in 80 pL of dilution buffer (2% BSA/0.1% Triton X-100/TBS, pH 7.2-7.4) and samples were added to sub-arrays and designated for standards on the slide, then incubated for 1 hour at RT. After incubation, slides were washed 4 times, 3 min. each time. The detector Abs were added in 80 μL of the reaction buffer and incubated for 2 hours at RT. After unbound secondary detector Abs were removed by washing with TBST, 80 μL of biotin-tyramide (400 μg/mL in ethanol, Perkin Elmer Life Science) at 5 μg/ml in 50 mM glucose/PBS was added and incubated for 15 min in the dark. The GO-HRP channeled tyramide-mediated signal amplification process was terminated by washing with TBST 4 times for 3 min each. The local deposition of biotin-tyramide was detected by adding streptavidin (SA)-Alexa647 (in PBS, Invitrogen) at 0.5 μg/ml (1:4000 dilution) in 2% BSA/0.1% Triton/TBS for 40 min. Upon completion of incubation, slides were washed 4 times with TBST, dried and kept in the dark until scanning on the microarray scanner.

tErbB2 (e.g., p95HER2) Enrichment: Full-length p185-ErbB2 receptors were removed from cell lysates using magnetically labeled antibodies specific to the extracellular domain (ECD) of ErbB2. The resulting p185-ErbB2 depleted cell lysate contains t-ERBB2 receptor proteins lacking the ECD and subsequent analysis were performed to quantitate the level of t-ERBB2 expression and activation.

Clinical Samples: The flash frozen breast cancer tissues were purchased from ILSBio. All patients were Caucasian with ductal carcinoma at stage II or III. ErbB2-IHC status was available for all samples. The flash frozen tissue samples were lysed in 100 μL of lysis buffer. Lysed samples were kept on ice for 30 min and centrifuged. The protein concentrations of supernatants were determined by BCA protein assay kit (Pierce), and the resulting lysates were stored at −80° C. before subsequent analysis. FNA samples were collected from patients with progressive, measurable metastatic Stage IIIB, or Stage IV breast cancer, and who were about to start systemic therapy. Patients had histologically or cytologically confirmed invasive breast cancer. The FNA samples were collected using G23 gauge needles. FNA samples were immediately injected into collection vials containing lysis buffer and were shipped over night for subsequent analysis.

IP-Western Blotting: The cell lysates were incubated with magnetic beads conjugated with antibodies against the ICD of ERBB2 overnight on a rocker at 4° C. The immuno-magnetically enriched lysates were resuspended in sample buffer containing P3-mercaptoethanol, boiled for 5 min, cooled to RT and loaded onto a NuPage (Invitrogen) 4-12% gel. Upon completion, the separated proteins were transferred to a nitrocellulose membrane, then washed, blocked with 5% milk blotto, and incubated with the 1° then 2° Abs before the detection process using NBT/BCIP.

CEER Data Analysis: Each slide was scanned at three photomultiplier (PMT) gain settings to increase the effective dynamic range. Background-corrected signal intensities were averaged for replicate spots printed in triplicate. The relative fluorescence value of the respective reagent blank was subtracted from each sample. Several quality criteria were used to filter data from further analysis including limits on the spot footprint, coefficient of variation for spot replicates, overall pad background and the intensity of the reagent blank. For each assay, a standard curve was generated from serially diluted cell lysates prepared from BT474 cells. Data was fit to a five parameter equation derived as a function of capture antibody concentration and PMT. Each curve was plotted as a function of log signal intensity, measured as relative fluorescence unit (RFU) vs. log concentration and referenced to the standard cell line, BT474. The individual predictions from each dilution and gain were averaged into a single, final prediction.

Results

Figure 4:
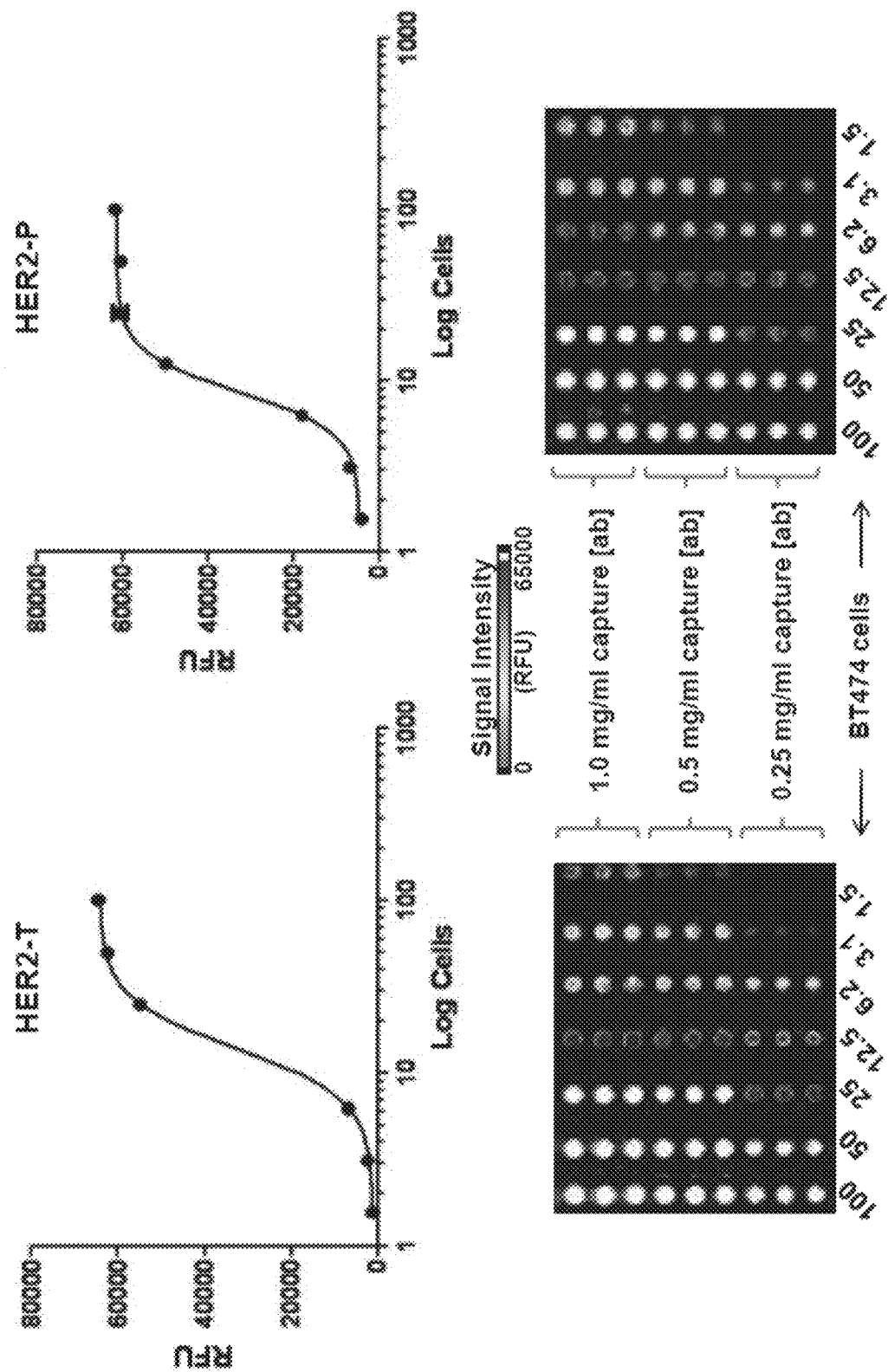
FIG. 4 shows titration curves generated from CEER for ERBB2-T and ERBB2-P. These values are used as standards to generate quantitative values for clinical samples.
Figure 5:
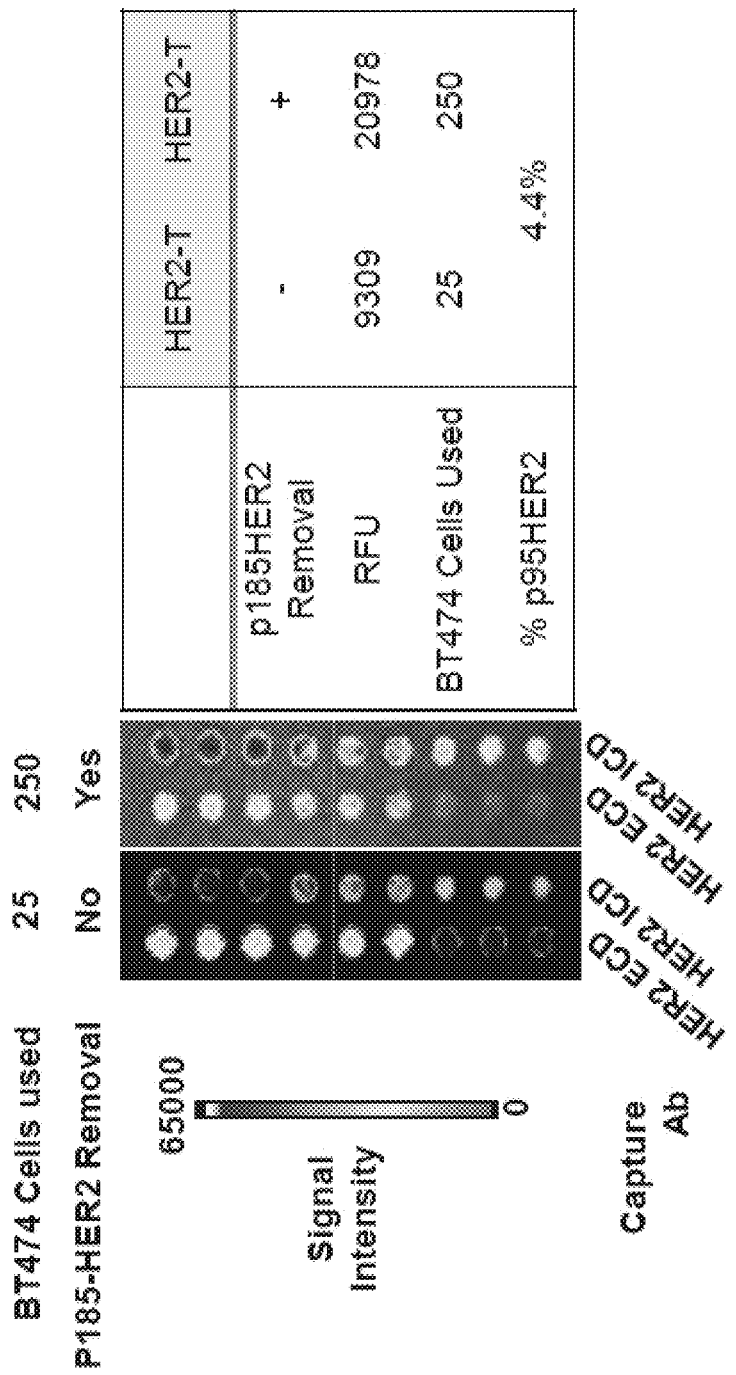
FIG. 5 shows the determination of t-ERBB2 in BT474 cells. The ERBB2-CEER assay was performed using cell lysates prepared from BT474 cells. The full-length p185-ERBB2 assay was determined from lysates containing ~25 BT474 cells and the level of t-ERBB2 was determined by analyzing cell lysates prepared from ~250 BT474 cells post immuno-magnetic removal of p185-ERBB2.

Expression of t-ERBB2s in human cells and tumors. To assess the levels and activation of ERBB2 isoforms in human cells and tumor samples, CEER, a novel antibody capture and proximity based immune-microarray platform, was employed (FIG. 3). CEER requires an immuno-complex formation between the target-specific capture antibody and two additional detector antibodies. One of the detector antibodies is conjugated with Glucose Oxidase (GO) and the other is conjugated with Horseradish Peroxidase (HRP). The detector antibodies can bind to either two different epitopes (which determines the target expression level) or to a phosphorylated domain on the captured protein and one alternative epitope (which determines the target activation level). When GO in the immune-complex is supplied with a substrate such as glucose, it generates hydrogen peroxide ($H_2O_2$) which is channeled to the co-localized HRP, thereby enhancing the analytical sensitivity. As the assay configuration requires a successful immuno-complex formation between multiple capture/detector antibodies, the platform provides the specificity necessary for simultaneous analysis on multiple target proteins. As shown in FIG. 4, this method is able to detect total and phosphorylated ERBB2 in BT474 cell lines with single digit analytical sensitivity. The comparison of the differential ERBB2 profiling (with ERBB2-ECD and ERBB2-ICD captures) of BT474 cells with and without the removal of the full-length p185-ERBB2 showed that there was approximately 4.4% t-ERBB2 (or ~52800 tERBB2 receptors/cell) in this ERBB2 amplified cell line with approximately $1.2 \times 10^6$ ERBB2 receptors/cell (FIG. 5).

Frozen breast tumor samples from 74 patients were scored for ERBB2 levels using immunohistochemical analysis and were then analyzed using CEER (Table 3). Of the 74 samples, 24 were ERBB2 low/negative (score=0-1 by IHC), 19 had moderate ERBB2 expression (score=2), and the remaining 31 had high expression of ERBB2 (score=3). By CEER analysis, none of the ERBB2 low or negative tumors expressed a significant level of truncated ERBB2, as expected. The levels of ERBB2 and t-ERBB2 and phosphorylated t-ERBB2 in each sample (shown in RTK molecules/cell in reference to BT474 cells) are summarized in the Table 2. However, 10% (2 of 19) moderate ERBB2-positive tumors expressed t-ERBB2, and 52% (16 of 31) strongly ERBB2-positive tumors expressed t-ERBB2. Furthermore, t-ERBB2 isoforms were phosphorylated in both moderately ERBB2-positive tumors (10%, 2 of 19 samples) and high-ERBB2 tumors (32%, 10 of 31). There were samples with significant levels of tERBB2 phosphorylation and only moderate levels of t-ERBB2 (20330 and 24913), and this may be possible as t-ERBB2 can be activated through interaction with other RTKs. Examples of tumor CEER-ERBB2 profiling and IP-Western analysis of ERBB2 are provided in FIG. 6 (samples are underlined in Table 2) and FIG. 7 (samples are italicized in Table 2), respectively. In addition, FNAs from metastatic sites of 8 breast cancer patients were analyzed. Three samples with ERBB2-positive disease showed varying degree of t-ERBB2 and phosphorylated t-ERBB2 (Table 3) while samples from ERBB2 negative cancers did not show t-ERBB2 expression. On expanded RTK profiling, IGF1R and c-MET expression was detected in 8C3-005-006, and this may be the cause for higher level of pt-ERBB2 despite lower level of t-ERBB2 among ERBB2 positive FNA samples.

TABLE 1

Expression and phosphorylation of t-ERBB2 in human breast tumors.

| IHC | ERBB2 score 0/1 | ERBB2 score 2 | ERBB2 score 3 |
|---|---|---|---|
| sample # | 24 | 19 | 31 |
| COPIA t-ERBB2+ | 0 | 2 | 16 |
| COPIA t-ERBB2-P+ | 0 | 2 | 10 |
| % t-ERBB2+ | 0% | 11% | 52% |
| % t-ERBB2+ | 0% | 11% | 32% |

TABLE 2

ERBB2 profiling of breast cancer tissue.

| Sample | IHC | p185HER2-T (RTK/cell) | tHER2-T (RTK/cell) | tHER2-P (pRTK/cell) |
|---|---|---|---|---|
| 24315 | 3 | 1,253,211 | 31,342 | 247 |
| 20013 | 3 | >2 ×10e6 | 74,298 | 150 |
| 25066 | 3 | 1,876,717 | 62,646 | 162 |
| 26110 | 3 | >2 × 10e6 | 75,942 | 1,007 |
| *26115* | 3 | >2 × 10e6 | 314,177 | 3,565 |
| *20250* | 3 | 1,108,050 | 41,569 | 81 |
| *24289* | 3 | >2 ×10e6 | 52,315 | 297 |
| 20012 | 3 | 1,840,292 | 75,450 | 1,289 |
| *24300* | 3 | 1,501,949 | 154,422 | 371 |
| 20003 | 3 | 1,227,092 | 44,179 | 566 |
| 19730 | 3 | 1,753,386 | 126,745 | 390 |
| OV8S1 | 3 | 937,546 | 25,552 | 41 |
| *20323* | 3 | >2 × 10e6 | 107,268 | 6,464 |
| 20520 | 3 | >2 × 10e6 | 113,161 | 3,687 |
| 21704 | 3 | 1,520,673 | 48,669 | 93 |
| 26811 | 3 | >2 × 10e6 | 307,337 | 4,523 |
| 26106 | 3 | >2 × 10e6 | 125,062 | 935 |
| 22080 | 3 | 1,340,073 | 142,055 | 2,215 |
| 19844 | 3 | 956,628 | 49,042 | 158 |
| 20371 | 3 | >2 × 10e6 | 105,413 | 728 |
| AUBBG | 3 | 486,835 | 15,525 | 56 |
| 22715 | 3 | 1,148,445 | 58,781 | 3,467 |
| 21703 | 3 | 643,236 | 31,597 | 92 |
| 19927 | 3 | 1,452,313 | 91,566 | 563 |
| 20330 | 3 | 458,839 | 45,080 | 1,251 |
| 21657 | 3 | 292,283 | 10,048 | 28 |
| 22610 | 3 | 745,833 | 39,916 | 195 |
| 24720 | 3 | 511,344 | 28,431 | 524 |
| 26775 | 3 | 664,308 | 36,527 | 397 |
| 25058 | 3 | 655,416 | 86,973 | 5,506 |
| 19871 | 3 | 223,808 | 25,221 | 235 |
| 22113 | 2 | >2 × 10e6 | 66,497 | 724 |
| ZCCFFAK4 | 2 | 433,513 | 13,746 | 135 |
| 26773 | 2 | 946,789 | 208,282 | 16,141 |
| 26780 | 2 | 538,384 | 7,338 | — |
| *24913* | 2 | 393,028 | 36,054 | 2,145 |
| 25283 | 2 | 118,612 | 7,000 | 25 |
| *24298* | 2 | — | — | — |
| 26379 | 2 | 221,142 | 6,468 | 52 |
| WUQT6 | 2 | 314,653 | 17,864 | 47 |
| 25882 | 2 | 219,387 | 3,026 | 93 |
| *25897* | 2 | 137,399 | 10,424 | 248 |
| 24960 | 2 | — | 15,563 | 43 |
| 26154 | 2 | 110,091 | 3,511 | 111 |
| 25061 | 2 | — | 8,993 | 105 |
| 22176 | 2 | — | 3,788 | 95 |
| 21962 | 2 | — | 1,515 | 102 |
| *24708* | 2 | — | 4,769 | 16 |
| 20525 | 2 | — | 1,806 | 50 |
| 24916 | 2 | — | 2,224 | 15 |
| 26814 | 1 | 313,244 | 2,861 | 72 |
| 22090 | 1 | 291,607 | 3,481 | 35 |
| 22112 | 1 | — | — | — |
| 24272 | 1 | 116,945 | 20,619 | 265 |
| 19875 | 1 | — | 5,448 | 110 |
| 19924 | 1 | — | 4,123 | 15 |
| 20014 | 1 | — | 10,040 | 43 |
| 26371 | 1 | — | 13,302 | 469 |
| *24914* | 1 | — | — | — |
| 24400 | 1 | — | 10,078 | 93 |
| 26776 | 1 | — | 346 | — |
| 19826 | 1 | — | 21,840 | 75 |
| 24931 | 1 | — | 8,054 | 95 |
| KW7YHAET | 1 | — | 3,367 | 36 |
| NP11802 | 1 | — | 2,053 | 17 |
| 19898 | 1 | — | 894 | — |
| 21655 | 0 | 13,941 | 11,983 | 65 |
| 24676 | 0 | — | 2,905 | — |
| *19895* | 0 | — | 8,896 | 214 |
| 19692 | 0 | — | 2,664 | 50 |
| *17253* | 0 | — | — | — |
| 20007 | 0 | — | 5,536 | 52 |
| *21663* | 0 | — | 4,463 | 44 |
| 1R2H7 | 0 | — | — | 66 |

Figure 6:
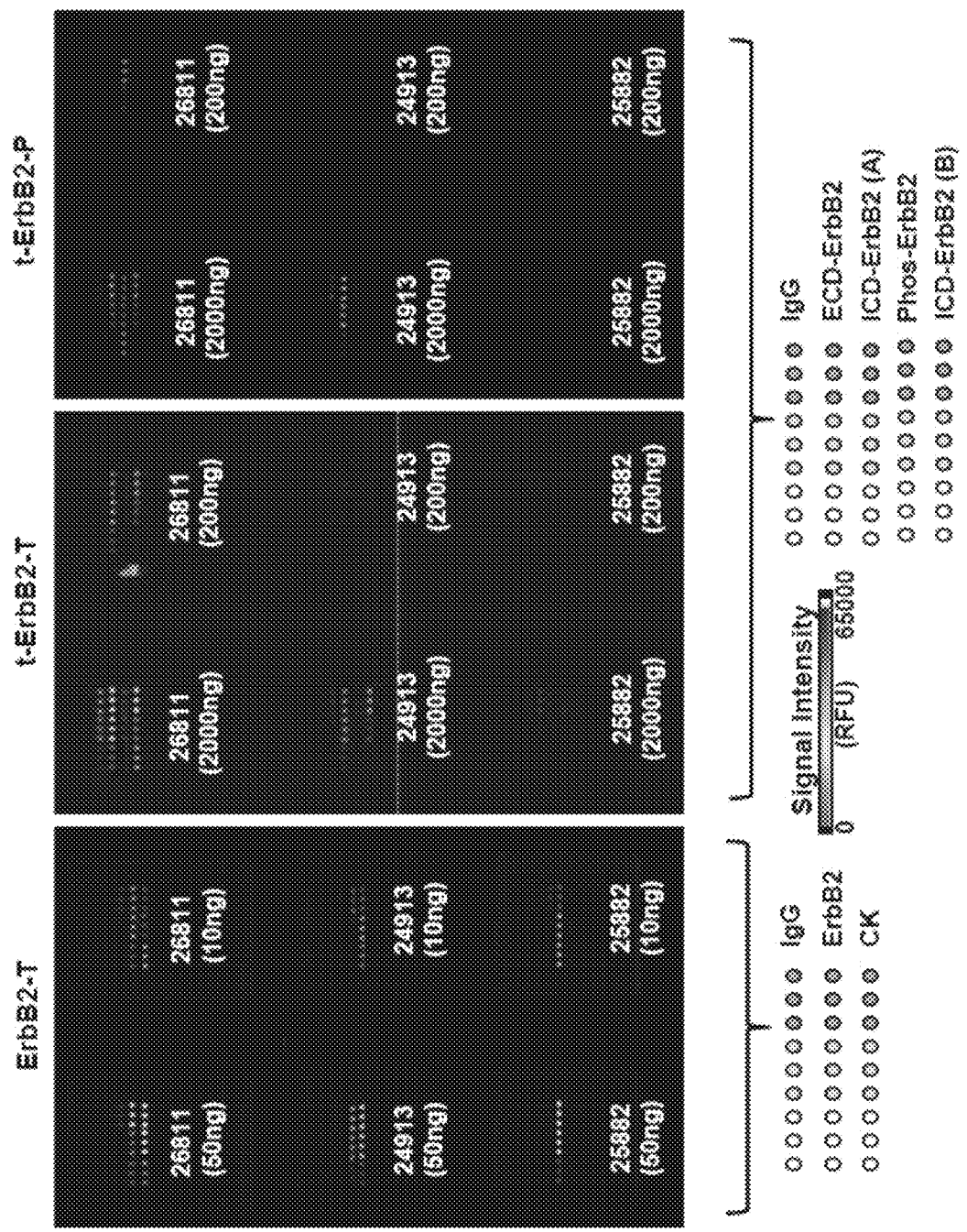
FIG. 6 shows the expression and phosphorylation of t-ERBB2s in patient tumors. ERBB2, t-ERBB2, phosphorylated t-ERBB2. The array configuration is indicated. CEER not only allows differentiation of full-length vs. truncated ERBB2 expression in clinical samples, but also provides valuable information on the level of phosphorylation in a quantitative manner.
Figure 7:
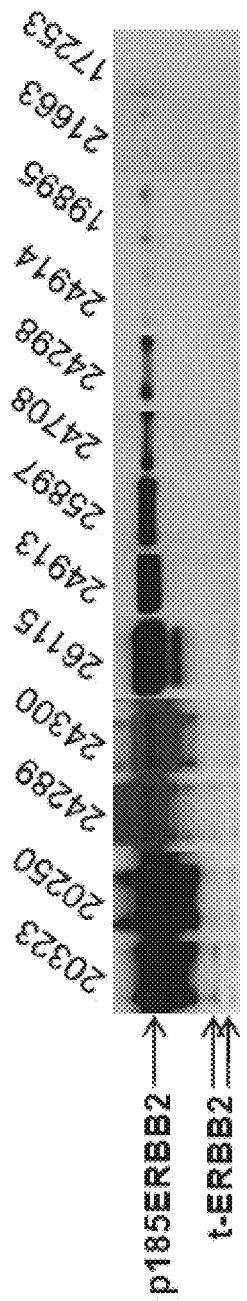
FIG. 7 shows an exemplary IP-Western for ERBB2 for clinical samples. Anti-ICD-ERBB2 antibodies were used to immuno-precipitate ERBB2 receptors and subsequent Western blot analysis was performed using second anti-ICD-ERBB2 antibodies to differentiate full-length t-ERBB2 from full-length p185-ERBB2.

The exemplary CEER array images are shown for the underlined samples in FIG. 6 and the IP-Western blot for the italicized samples are shown in FIG. 7. The RTK/cell values are determined by comparing the input amount of samples and equivalent amount of standard BT474 cells.

TABLE 3 t-ERBB2 analysis for FNA samples.

| Sample ID | t-ERBB2 (RTK/cell) | pt-ERBB2 (pRTK/cell) |
|---|---|---|
| 8C3-002-001 | 57,341 | 3,062 |
| 8C3-005-006 | 26,989 | 5,309 |
| 8C3-005-007 | 50,741 | 5,204 |

Figure 8:
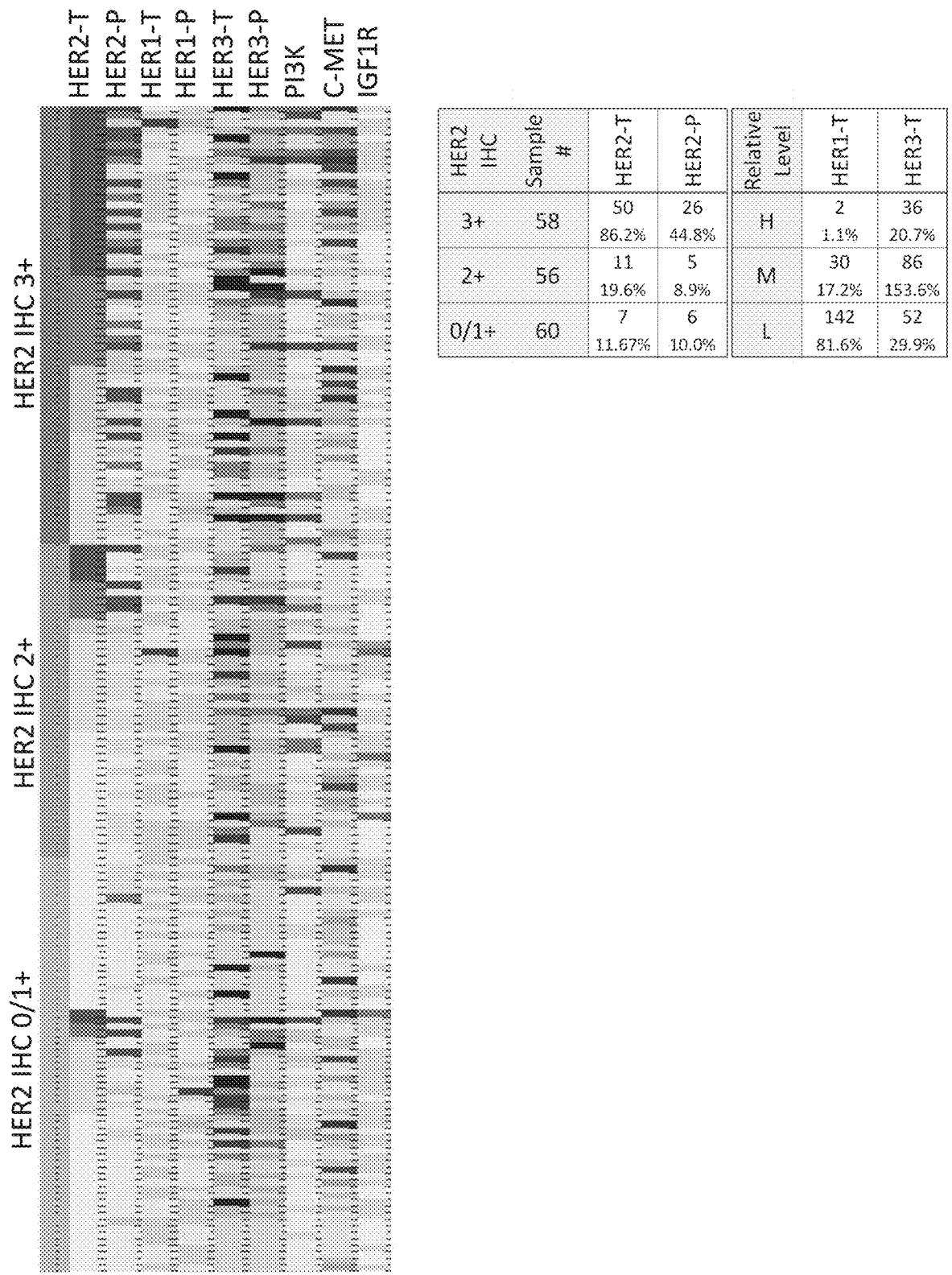
FIG. 8 shows that a wide range of pathway protein expression and activation in 174 BCA samples was observed.

A wide range of pathway protein expression and activation in 174 BCA samples was observed as shown in FIG. 8. The sample with the highest signal for each marker is indicated with the darkest color. The CEER-HER2 showed high correlation with IHC-HER2 status. Discordant HER2 status between CEER and IHC was resolved by IP-Western and showed >98% correlation. The HER3-P level showed high degree of correlation with HER3-T and PI3K activation. The cMET profile also showed strong correlation with PI3K activation. 27% (12/45 of 2+ by IHC) and 21% (11/53 of 0/1+ by IHC) of BCA tissues with non-overexpressing but with significant levels of HER2 showed over 5% phosphorylation of expressed HER2 receptor.

Conclusion

The status of HER2 and its variant forms as well as other RTKs provides critical information on the potential mechanisms for HER2-positive BCA patients who do not respond to trastuzumab due to either primary or acquired resistance. The CEER analysis described herein can be utilized to profile BCA patients for their signal transduction proteins for selecting an effective targeted therapy.

Example 5. Comprehensive Pathway Profiling to Predict Response to Therapy in Triple-Negative Metastatic Breast Cancer (TNMBC)

Improved therapies and predictive markers are needed in TNBC. This study used core-biopsy specimens from triple negative breast cancer patients treated with B (Avastin® [bevacizumab]), C (Carboplatin), and nabP (Abraxane®) ("triplet therapy") to (1) determine the level of expression and activation of various signaling pathway proteins in TNMBC (e.g., VEGFR2, c-KIT, HER1, etc.) and (2) correlate these expression and activation patterns in TNMBC with response.

Figure 9:
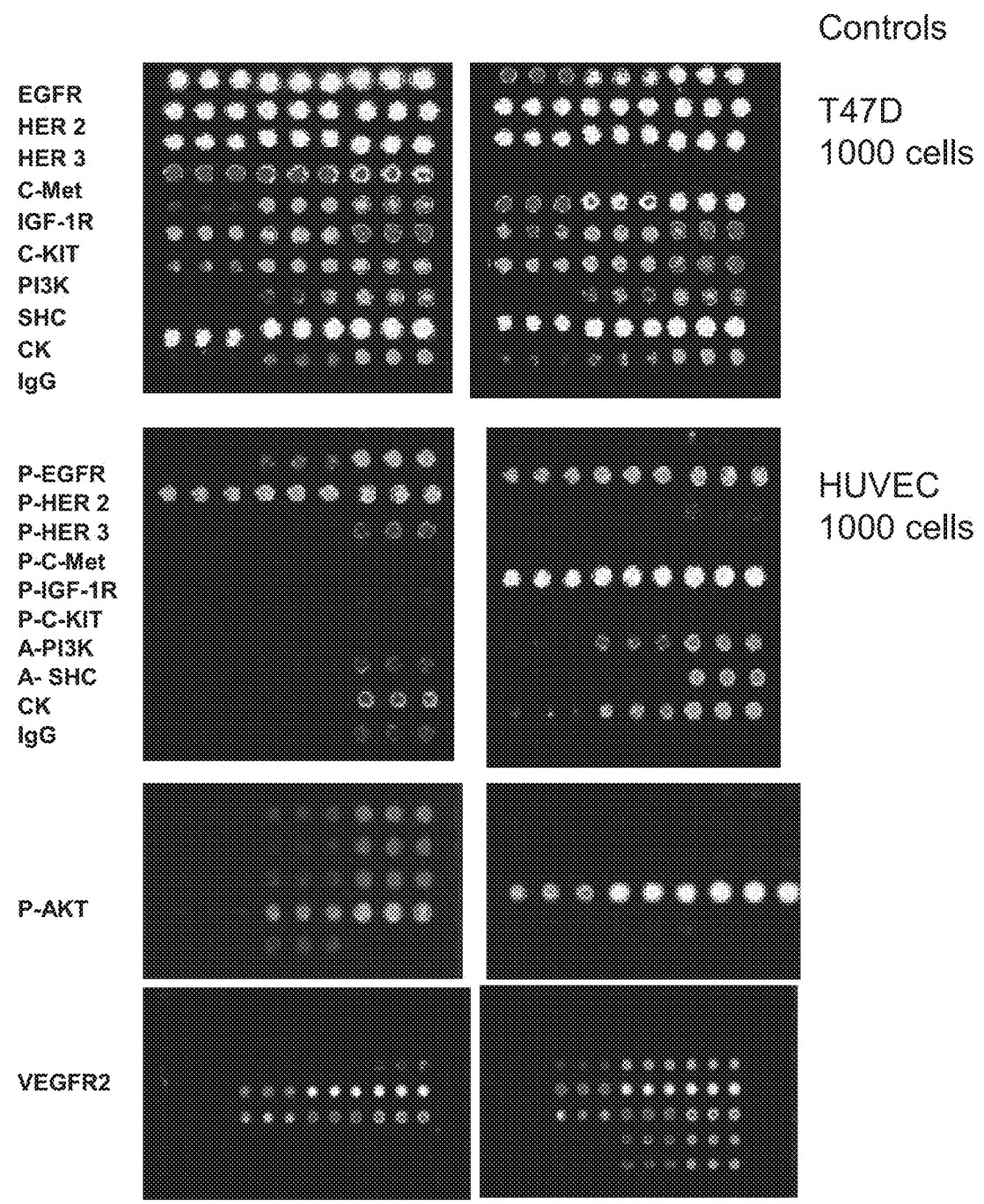
FIG. 9 shows an example of functional pathway profiling by CEER on a triple negative breast cancer core-biopsy sample compared to control T47D breast cancer cells and human umbilical vein endothelial cells (HUVEC).

Triple negative breast cancer core-biopsy samples (n=17) obtained from patients prior to starting treatment with B (Avastin® [bevacizumab]), C (Carboplatin), and nabP (Abraxane®) were collected and appropriately frozen at −80° C. A novel immunoassay method was applied to investigate the levels of expression and activation of signaling proteins in 1000 ng to 5000 ng of frozen tissues. The Collaborative Enzyme Enhanced Reactive ImmunoAssay (CEER) (also known as the COllaborative Proximity ImmunoAssay (COPIA)) as described herein is a multiplexed immuno-microarray platform that utilizes the formation of a unique immuno-complex requiring the co-localization of two detector antibodies for channeling events to achieve signal generation/amplification that results in extremely high analytical sensitivity and specificity. FIG. 9 provides an example of functional pathway profiling by CEER on a triple-negative breast cancer core-biopsy sample compared to control T47D breast cancer cells and human umbilical vein endothelial cells (HUVEC). In particular, the expression and activation of the following signaling pathway proteins in TNMBC were evaluated by CEER: EGFR (HER1), HER2, HER3, c-Met, IGF-1R, c-KIT, PI3K, SHC, AKT, and VEGFR2.

Progression Free Survival (PFS) was also determined. For each marker, samples were split into "high" and "low" groups based on a cutoff value. For example, the cutoff value can be selected at or close to the median to equalize group sizes (e.g., 8=low, 9=high). The parametric t-test test was used to correlate protein expression and activation with PFS. The PFS was compared for the low (e.g., below median) versus high (e.g., above median) groups. FIG. 10 illustrates the results of such a comparison between the PFS for the low and high sample groups for each marker. In particular, the table in FIG. 10 shows that low c-KIT or low VEGFR2 expression is associated with a significantly longer duration of PFS compared to higher levels of that marker (42.1 weeks PFS for low total c-KIT levels versus 20.7 weeks PFS for high total c-KIT levels; 39.9 weeks PFS for low total VEGFR2 levels versus 20.9 weeks PFS for high total VEGFR2 levels). The table in FIG. 10 also shows that low IGF-1R activation, low c-KIT activation, low IGF-1R expression, and low HER1 activation were each associated with longer duration of PFS compared to higher levels of that marker. In addition, the table in FIG. 10 shows that high HER1 expression is associated with a longer duration of PFS compared to lower levels of that marker (36.8 weeks PFS for high total HER1 levels versus 23.4 weeks PFS for low total HER1 levels). The table in FIG. 11 illustrates a similar analysis using a nonparametric Wilcoxon rank sum test to correlate protein expression and activation with PFS. Low c-KIT or VEGFR2 expression was again shown to be associated with a significantly longer duration of PFS compared to higher levels of that marker.

Figure 12:
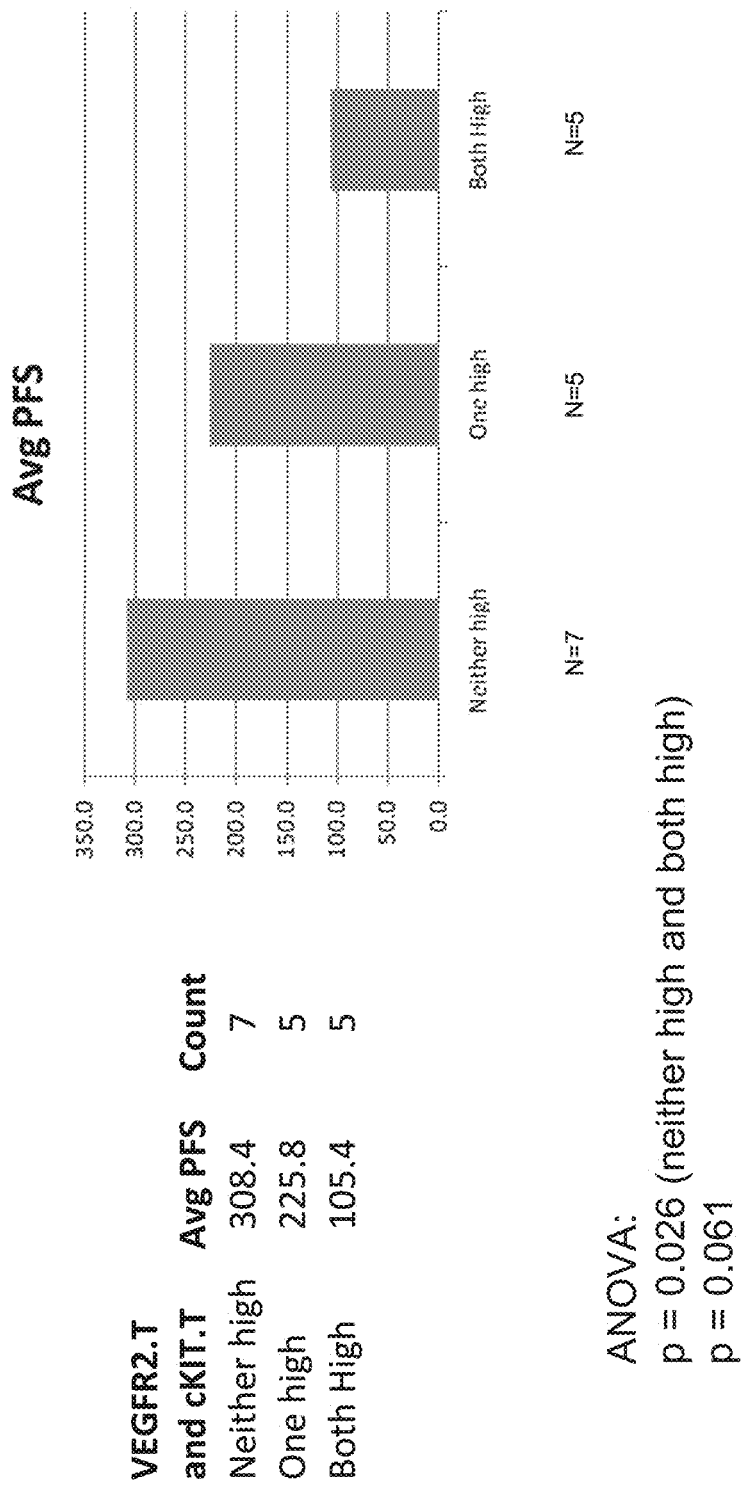
FIG. 12 shows that measuring the expression levels of both c-KIT and VEGFR2 increases the predictive value of determining response to triplet therapy in TNMBC.

FIG. 12 shows that measuring the expression levels of both c-KIT and VEGFR2 increases the predictive value of determining response to triplet therapy in TNMBC. In particular, a combination of low c-KIT and VEGFR2 expression levels ("Neither high") was found to be associated with a significantly longer duration of PFS compared to samples in which one or both markers were high ("One high" or "Both high").

Figure 13:
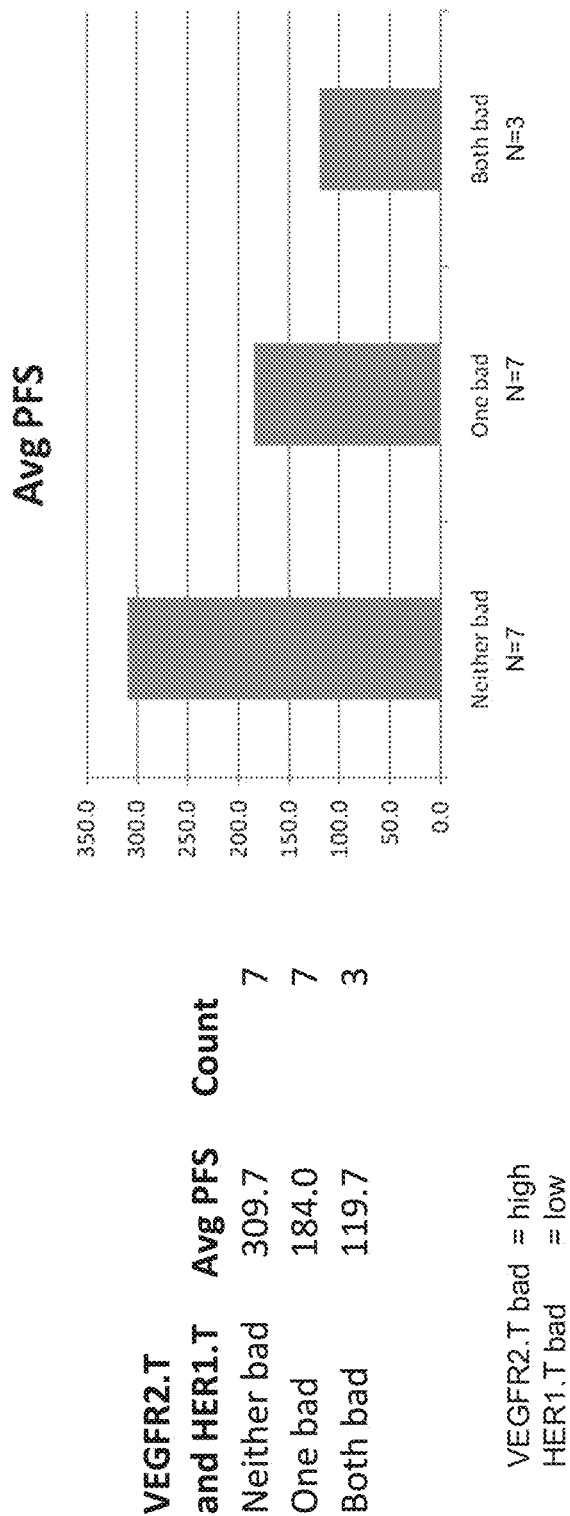
FIG. 13 shows that measuring the expression levels of both VEGFR2 and HER1 increases the predictive value of determining response to triplet therapy in TNMBC.

FIG. 13 shows that measuring the expression levels of both VEGFR2 and HER1 increases the predictive value of determining response to triplet therapy in TNMBC. In particular, a combination of high HER1 and low VEGFR2 expression levels ("Neither bad") was found to be associated with a significantly longer duration of PFS compared to samples in which HER1 expression was low and/or VEGFR2 expression was high ("One bad" or "Both bad").

Figure 14:
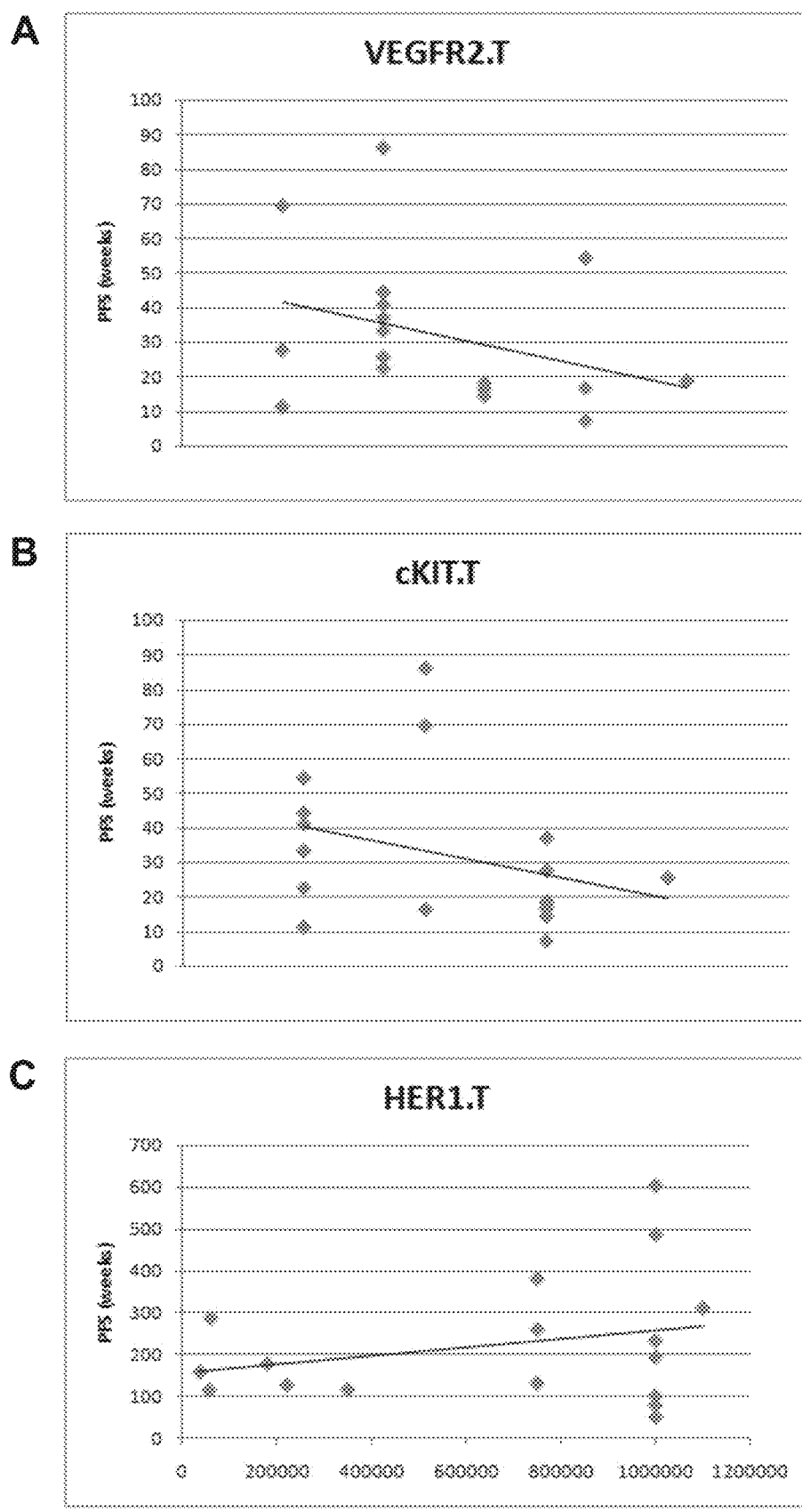
FIG. 14 shows the correlation between increasing levels of (A) total VEGFR2, (B) total c-KIT, and (C) total HER1 and response to triplet therapy.

FIG. 14 illustrates the correlation between increasing levels of (A) total VEGFR2, (B) total c-KIT, and (C) total HER1 and response to triplet therapy, as indicated by the length of PFS. In particular, lower total VEGFR2 or c-KIT levels were associated with response to triplet therapy in TNMBC, whereas higher total HER1 levels were associated with response to triplet therapy in TNMBC.

In conclusion, this example demonstrates that: (1) there is a correlation between activated (phospho) and total levels for both c-KIT and IGF-1R; (2) low VEGFR2 or c-KIT expression levels are predictive of response; (3) high EGFR (e.g., should respond to platinum based therapies) expression levels correlate with response, while high P-EGFR levels do not; (4) in general, if pathway activation (e.g., P-c-KIT, p-IGF-1R, p-EGFR, p-AKT, and others) is low (e.g., not highly proliferative tumor), the patient has a higher PFS to triplet therapy of Carboplatin, Nab-Pactitaxel, and Avastin®; and (5) for combination therapeutics, the addition of total VEGFR2 expression to total c-KIT or EGFR expression results in better predictive values.

Example 6. Tumor Tissue Collection and Processing

Tumor tissue or FNA samples may be obtained from patients with cancer for signal transduction pathway interrogation using the proximity assays described herein (e.g., CEER). For example, samples for pathway analysis can be obtained from frozen tissues either by sectioning or performing a frozen FNA procedure. In certain instances, tissue sectioning is performed on frozen specimens for subsequent profile analysis. In certain other instances, the relatively non-invasive FNA procedure is performed for obtaining samples from patients (and xenografts) in a clinical environment.

Frozen tissue samples may be collected by the following methods:

Option #1. Tissue Section Collection:
1. Keep a plastic weighing boat on dry ice, in which sample cutting will take place.
    a. To chill the materials, keep razor blades or microtome blades, fine forceps, and pre-labeled sample collection vials on dry ice.

2. Take frozen human cancer tissues from −80° C. freezer and transfer samples immediately onto dry ice.
3. Place frozen tissue to weighting boat on dry ice, cut small pieces of frozen tissue (10 μm section×3) using razor blade or microtome blade, and transfer the tissue into pre-chilled and pre-labeled sample collection vial using pre-chilled forceps.
4. Close cap and keep it on dry ice.
5. Place collected specimens into a double plastic bag first and then into a STYROFOAM™ container (primary container) with adequate amount of dry ice.
   a. Use at least 6-8 pounds dry ice. Use more in the summer months.
      NOTE: Exact amount of dry ice will be determined after consulting with a shipping company.
   b. Consult with shipping company for the international shipping process for necessary permits and documentations.
   c. Do not use wet ice, or coolants (i.e., Cool Packs).
6. Make certain the requisition and sample list is placed in the box, but on the outside of the double bag.
7. Securely seal the container and label "Frozen Tissue—Do Not Thaw."

Option #2. FNA Prep from Frozen Tissues:
1. Take frozen human cancer tissues from −80° C. freezer and transfer sample vials immediately on dry ice.
2. Samples ready for FNA procedure should be placed on wet ice for 10 minutes to soften the tissue.
3. FNA sample collection should be performed by passing a 23 or 25 gauge needle through softened frozen tissue 5 to 10 times. Return remaining sample vial to dry ice.
4. Wipe the FNA sample collection vial lid with alcohol.
5. Frozen FNA tissues should be collected by direct injection into the collection vial containing 100 μl of "protein later solution" (Prometheus Laboratories; San Diego, Calif.). Dispense collected tissue materials by gently mixing the content.
6. Hold the FNA collection vial firmly with one hand and perform rapid finger tapping (~15×) to ensure through cell lysis (vortex for 10 seconds if possible).
7. Place collected specimens into a double plastic bag first and then into a STYROFOAM™ container (primary container) with Cool Packs.
   a. Consult with shipping company for the international shipping process for necessary permits and documentations.
8. Make certain the requisition and sample list is placed in the box, but on the outside of the double bag.
9. Securely seal the container and label with "Biological Specimen."

Example 7. Data Analysis for Quantitation of Signal Transduction Pathway Proteins in Cancer Cells This example illustrates the quantitation of the expression and/or activation levels of one or more analytes such as one or more signal transduction proteins in a biological sample (e.g., blood or tumor tissue) against a standard curve generated for the particular analyte of interest.

In some embodiments, each CEER slide is scanned at three photomultiplier (PMT) gain settings to improve sensitivity and reduce the impact of saturation. Perkin Elmer ScanArray® Express software is used for spot finding and signal quantitation. The identifiers for each spot are imported from a GenePix® Array List (.gal) file. The de-identified study specific number for each clinical sample on a slide is incorporated into the resulting data set.

In other embodiments, background corrected signal intensities are averaged for replicate spots printed in triplicate. The relative fluorescence value of the respective reagent blank is subtracted from each sample. Several quality criteria are used to filter data from further analysis including limits on the spot footprint, coefficient of variation for spot replicates, overall pad background and the intensity of the reagent blank.

For each assay, a sigmoidal standard curve can be generated from multiple (e.g., two, three, four, five, six, seven, etc.) concentrations of serially diluted cell lysates prepared from cell lines such as MD-468 (HER1 positive), SKBr3 (HER2 positive), BT474 (HER2 and p95HER2 positive), HCC827 (c-MET and HER1 positive), T47D stimulated with IGF (IGF1R positive), and/or T47D stimulated with HRG (HER3 positive). Each curve can be plotted as a function of signal intensity vs. log concentration derived units, CU (Computed Unit). The data can be fit to a five parameter equation (5PL) by nonlinear regression (Ritz, C. and Streibig, J. C., *J. Statistical Software*, 12, 1-22 (2005)), simultaneously fitting all three dilutions of the capture antibody. Fitting is carried out using R, an open source statistical software package (Development Core Team, R: A language and environment for statistical computing. R Foundation for Statistical Computing, Vienna, Austria. ISBN 3-900051-07-0 (2008)). To avoid over parameterization of the mathematical model and thereby improve accuracy, four parameters can be constrained, while each dilution can be solved for an individual inflection point. This process can be repeated for each PMT gain setting of 45, 50 and 60. This results in nine standard curves generated per assay, from three dilutions of capture antibody and three PMT scans. The built-in redundancy in the assay allows for one or more of the dilution/scan combinations to be eliminated if the fit of the standard curve has an $R^2$ less than 0.95 and thus improves subsequent predictions.

CU Calculation (based on standard curve)—The individual predictions from each of the standard curves (e.g., 3 capture antibody dilutions and 3 PMT gain-set scanning) can be combined into a single, final prediction. For each prediction, the slope of the point on the standard curve is calculated. This slope is taken with log-units on the x-axis, i.e., the units in the denominator of the slope are log Computed Units (CU). Second, a weighted average of the predictions is calculated, where the weights are determined from the slopes. Specifically, the weights are summed, and each point is given a weight equal to its slope divided by the total slopes. Each assay can be validated against predictions for known controls.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for determining whether a human subject with a triple-negative breast cancer will respond to therapy with a combination of bevacizumab, carboplatin, and paclitaxel, the method comprising:

(a) determining expression levels of c-KIT protein and VEGFR2 protein in a cellular extract of a breast tumor sample or a circulating tumor cell sample obtained from the human subject using a proximity immunoassay by contacting the cellular extract with (1) capture antibodies that bind to each of c-KIT protein and VEGFR2 protein, and (2) detection antibodies comprising first and second activation state-independent antibodies that bind to each of c-KIT protein and VEGFR2 protein;

(b) comparing the expression levels of c-KIT protein and VEGFR2 protein to median expression levels of c-KIT protein and VEGFR2 protein in a human population of triple-negative breast tumors; and (c) determining whether the human subject with a triple-negative breast cancer will respond to therapy with a combination of bevacizumab, carboplatin, and paclitaxel based on altered expression of c-KIT protein and VEGFR2 protein in the cellular extract relative to the median expression levels of c-KIT protein and VEGFR2 protein, wherein decreased expression of c-KIT protein relative to the median expression level of c-KIT protein and decreased expression of VEGFR2 protein relative to the median expression level of VEGFR2 protein is indicative of response to therapy with the combination of bevacizumab, carboplatin, and paclitaxel.

2. The method of claim 1, wherein the triple-negative breast cancer is triple-negative metastatic breast cancer.

3. The method of claim 1, wherein the paclitaxel is a nanoparticle albumin-bound (nab) paclitaxel.

4. The method of claim 1, wherein the breast tumor sample comprises a fine needle aspirate (FNA) sample.

5. The method of claim 1, wherein the capture antibodies are attached to a solid support.

6. The method of claim 5, wherein the first activation state-independent antibodies are labeled with glucose oxidase.

7. The method of claim 6, wherein the second activation state-independent antibodies are labeled with horseradish peroxidase.

8. The method of claim 7, wherein the binding of the first and second activation state-independent antibodies in proximity to each other generates a detectable signal.

9. A method for determining whether a human subject with a triple-negative breast cancer will respond to therapy with a combination of bevacizumab, carboplatin, and paclitaxel, the method comprising:

(a) determining expression levels of HER1 protein and VEGFR2 protein in a cellular extract of a breast tumor sample or a circulating tumor cell sample obtained from the human subject using a proximity immunoassay by contacting the cellular extract with (1) capture antibodies that bind to each of HER1 protein and VEGFR2 protein, and (2) detection antibodies comprising first and second activation state-independent antibodies that bind to each of HER1 protein and VEGFR2 protein;

(b) comparing the expression levels of HER1 protein and VEGFR2 protein to median expression levels of HER1 protein and VEGFR2 protein in a human population of triple-negative breast tumors; and (c) determining whether the human subject with a triple-negative breast cancer will respond to therapy with a combination of bevacizumab, carboplatin, and paclitaxel based on altered expression of HER1 protein and VEGFR2 protein in the cellular extract relative to the median expression levels of HER1 protein and VEGFR2 protein, wherein increased expression of HER1 protein relative to the median expression level of HER1 protein and decreased expression of VEGFR2 protein relative to the median expression level of VEGFR2 protein is indicative of response to therapy with the combination of bevacizumab, carboplatin, and paclitaxel.

10. The method of claim 9, wherein the triple-negative breast cancer is triple-negative metastatic breast cancer.

11. The method of claim 9, wherein the paclitaxel is a nanoparticle albumin-bound (nab) paclitaxel.

12. The method of claim 9, wherein the breast tumor sample comprises a fine needle aspirate (FNA) sample.

13. The method of claim 9, wherein the capture antibodies are attached to a solid support.

14. The method of claim 13, wherein the first activation state-independent antibodies are labeled with glucose oxidase.

15. The method of claim 14, wherein the second activation state-independent antibodies are labeled with horseradish peroxidase.

16. The method of claim 15, wherein the binding of the first and second activation state-independent antibodies in proximity to each other generates a detectable signal.

* * * * *